(12) United States Patent
Trocke et al.

(10) Patent No.: US 11,712,545 B2
(45) Date of Patent: Aug. 1, 2023

(54) LUBRICIOUS INSERTION TOOLS FOR MEDICAL DEVICES AND METHODS FOR USING

(71) Applicant: SURMODICS, Inc., Eden Prairie, MN (US)

(72) Inventors: Amy Trocke, Plymouth, MN (US); Gregg Sutton, Orono, MN (US); Joram Slager, Saint Louis Park, MN (US)

(73) Assignee: Surmodics, Inc., Eden Prairie, MN (US)

( * ) Notice: Subject to any disclaimer, the term of this patent is extended or adjusted under 35 U.S.C. 154(b) by 322 days.

(21) Appl. No.: 15/704,765

(22) Filed: Sep. 14, 2017

(65) Prior Publication Data

US 2018/0078744 A1 Mar. 22, 2018

Related U.S. Application Data

(60) Provisional application No. 62/464,520, filed on Feb. 28, 2017, provisional application No. 62/395,610, filed on Sep. 16, 2016.

(51) Int. Cl.
*A61M 25/10* (2013.01)
*A61M 25/06* (2006.01)
(Continued)

(52) U.S. Cl.
CPC .... *A61M 25/1002* (2013.01); *A61M 25/0668* (2013.01); *A61M 25/0097* (2013.01);
(Continued)

(58) Field of Classification Search
CPC ...... A61M 25/0668; A61M 2025/0046; A61M 2025/0047; A61M 2025/0048;
(Continued)

(56) References Cited

U.S. PATENT DOCUMENTS 4,195,637 A  4/1980 Gruntzig et al.
4,306,562 A * 12/1981 Osborne ........... A61M 25/0668
                                                  604/164.05

(Continued)

FOREIGN PATENT DOCUMENTS

JP   2006334222 A   12/2006
WO  2011/075727 A1   6/2011
(Continued)

*Primary Examiner* — Kami A Bosworth
(74) *Attorney, Agent, or Firm* — Kagan Binder, PLLC

(57) ABSTRACT

The disclosure provides insertion tools and articles that facilitate entry of a medical device, such as a balloon catheter, into the body, and that can provide advantages in terms of balloon insertion, safety, and drug delivery. The insertion tool includes a tubular portion that accommodates a balloon portion of a balloon catheter, and one or more separation margin(s) in the wall of the tubular portion or one or more split(s) in the tubular wall. The insertion tool also includes a proximal tab that extends from a second lengthwise half having a portion at an angle skew to the lengthwise axis, or that is in the form of a solid article comprising a concave surface that is fastened to an outer surface of the second lengthwise half of the tubular portion; or first and second tabs that extend from first and second lengthwise halves of the tubular portion, respectively.

20 Claims, 13 Drawing Sheets

(51) Int. Cl.
*A61M 25/00* (2006.01)
*A61M 39/06* (2006.01)

(52) U.S. Cl.
CPC ..... *A61M 39/06* (2013.01); *A61M 2025/1004* (2013.01); *A61M 2025/105* (2013.01); *A61M 2025/1079* (2013.01); *A61M 2025/1081* (2013.01); *A61M 2205/6081* (2013.01)

(58) Field of Classification Search
CPC .. A61M 2025/0062; A61M 2025/0675; A61M 2025/1004; A61M 2025/1081
See application file for complete search history.

(56) References Cited

U.S. PATENT DOCUMENTS

| | | | |
|---|---|---|---|
| 4,512,351 A * | 4/1985 | Pohndorf | A61N 1/0551 607/117 |
| 4,921,479 A | 5/1990 | Grayzel | |
| 4,983,168 A * | 1/1991 | Moorehead | A61M 25/0668 604/161 |
| 5,041,089 A | 8/1991 | Mueller et al. | |
| 5,087,246 A | 2/1992 | Smith | |
| 5,125,904 A * | 6/1992 | Lee | A61M 25/0668 604/161 |
| 5,250,033 A * | 10/1993 | Evans | A61M 25/0668 604/160 |
| 5,281,204 A * | 1/1994 | Horie | A61M 25/0668 604/164.05 |
| 5,312,355 A | 5/1994 | Lee | |
| 5,318,587 A | 6/1994 | Davey | |
| 5,382,234 A | 1/1995 | Cornelius et al. | |
| 5,569,294 A | 10/1996 | Parkola | |
| 5,571,089 A | 11/1996 | Crocker | |
| 5,766,203 A * | 6/1998 | Imran | A61F 2/958 604/103.08 |
| 5,776,101 A | 7/1998 | Goy | |
| 5,807,331 A | 9/1998 | den Heijer et al. | |
| 5,868,707 A * | 2/1999 | Williams | A61M 25/10 604/103 |
| 5,882,336 A | 3/1999 | Janacek | |
| 5,951,518 A * | 9/1999 | Licata | A61M 25/0668 604/161 |
| 6,080,141 A * | 6/2000 | Castro | A61M 25/0668 604/164.01 |
| 6,394,995 B1 | 5/2002 | Solar et al. | |
| 6,517,515 B1 | 2/2003 | Eidenschink | |
| 6,623,504 B2 | 9/2003 | Vrba et al. | |
| 6,758,854 B1 * | 7/2004 | Butler | A61M 25/0041 604/101.01 |
| 6,896,842 B1 | 5/2005 | Hamilton et al. | |
| 7,163,523 B2 | 1/2007 | Devens, Jr. et al. | |
| 8,951,545 B2 | 2/2015 | Arps et al. | |
| 9,180,226 B1 | 11/2015 | Jackson et al. | |
| 2004/0093005 A1 | 5/2004 | Durcan | |
| 2004/0172121 A1 | 9/2004 | Eidenschink et al. | |
| 2008/0183202 A1 | 7/2008 | Isham | |
| 2009/0030374 A1 | 1/2009 | Osypka | |
| 2010/0057176 A1 * | 3/2010 | Barker | A61N 1/0551 607/117 |
| 2010/0305509 A1 * | 12/2010 | Osypka | A61M 25/0668 604/164.05 |
| 2011/0208292 A1 | 8/2011 | Von Oepen et al. | |
| 2012/0071748 A1 * | 3/2012 | Mark | A61B 17/3417 600/411 |
| 2012/0296313 A1 * | 11/2012 | Andreacchi | A61M 25/0668 604/509 |
| 2013/0018309 A1 * | 1/2013 | Ewing | A61M 25/001 604/103.05 |
| 2013/0096604 A1 | 4/2013 | Hanson et al. | |
| 2015/0217092 A1 | 8/2015 | Kokate et al. | |
| 2016/0015934 A1 | 1/2016 | Okamura | |
| 2016/0058983 A1 | 3/2016 | Poker et al. | |
| 2017/0014601 A1 | 1/2017 | Kurosaki et al. | |

FOREIGN PATENT DOCUMENTS

| | | |
|---|---|---|
| WO | 2012/161994 A1 | 11/2012 |
| WO | 2014/179767 A2 | 11/2014 |
| WO | 2016/115361 A1 | 7/2016 |

\* cited by examiner

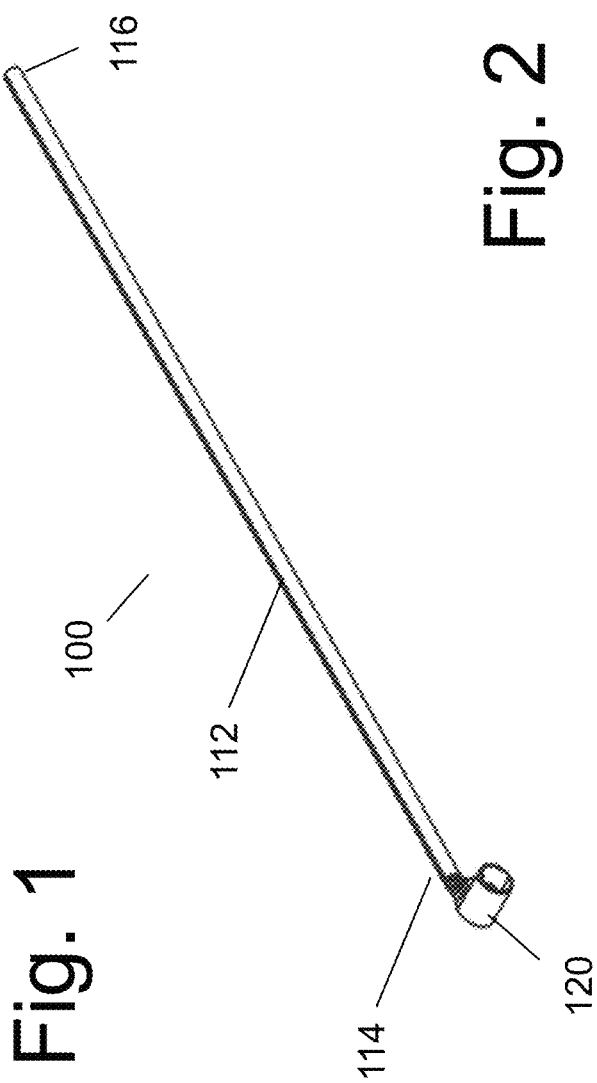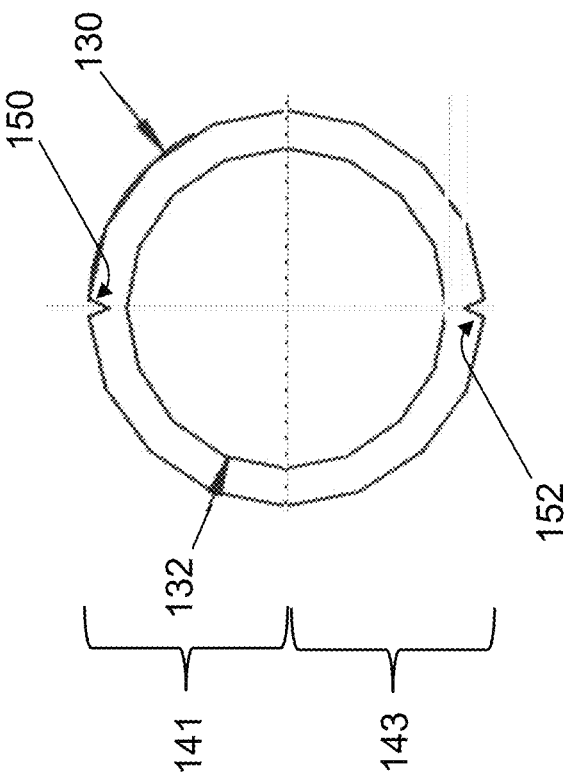

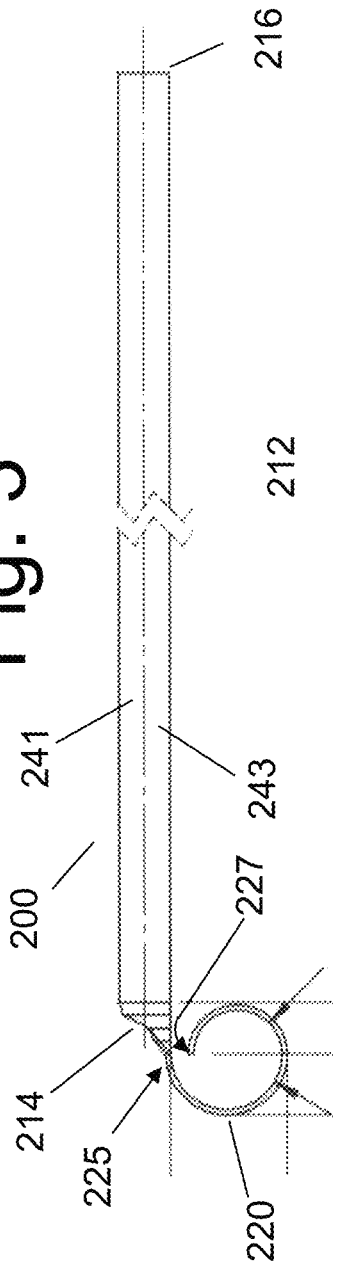
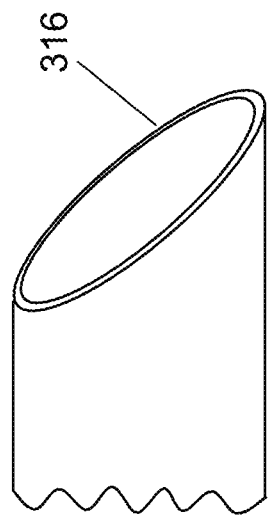

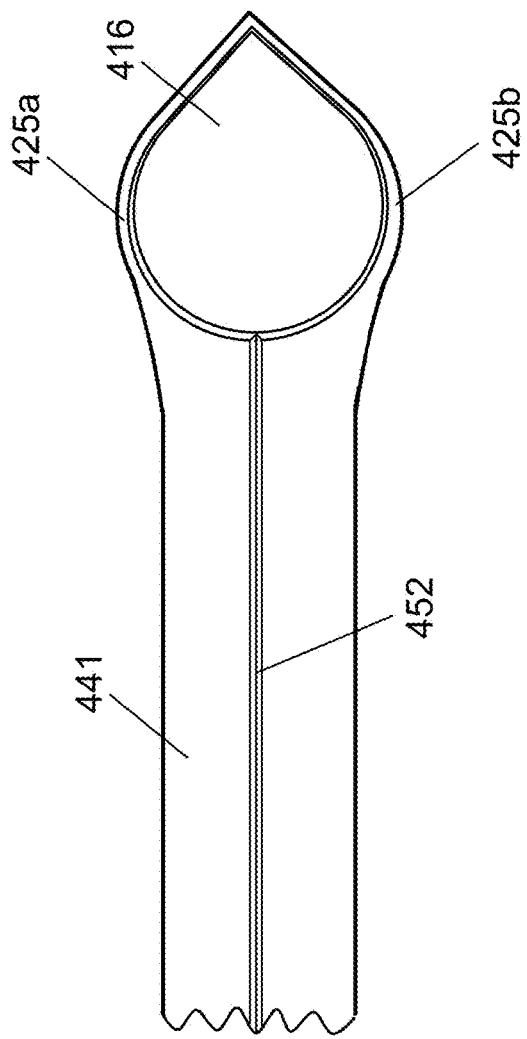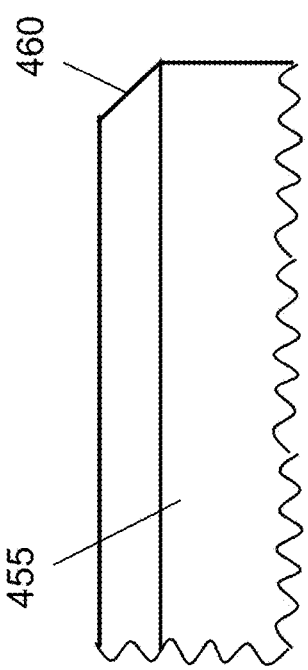

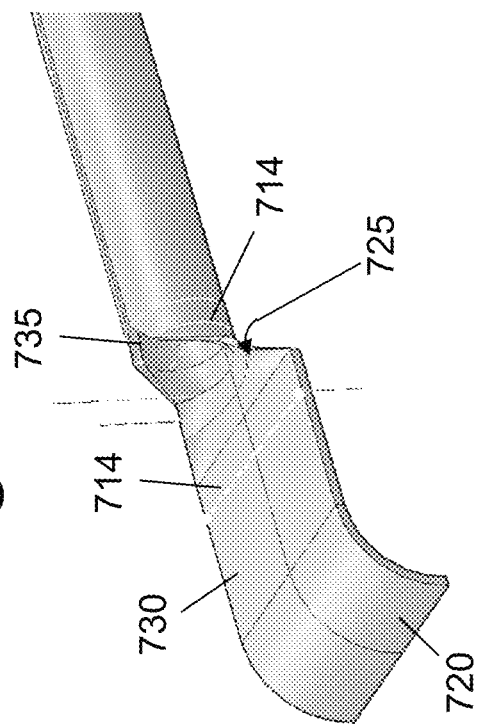
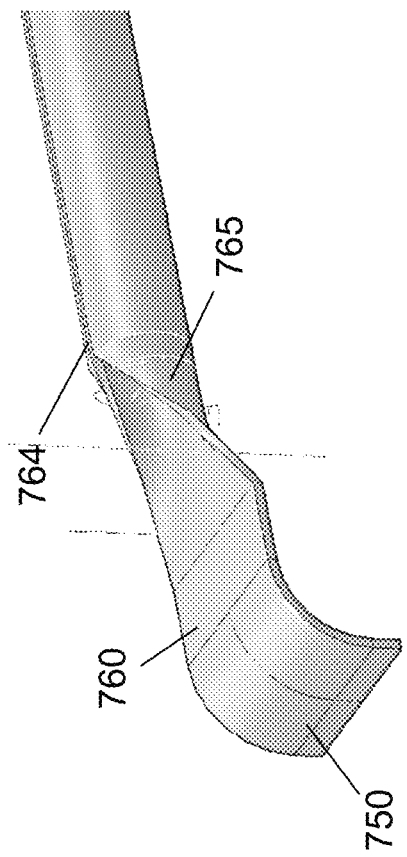

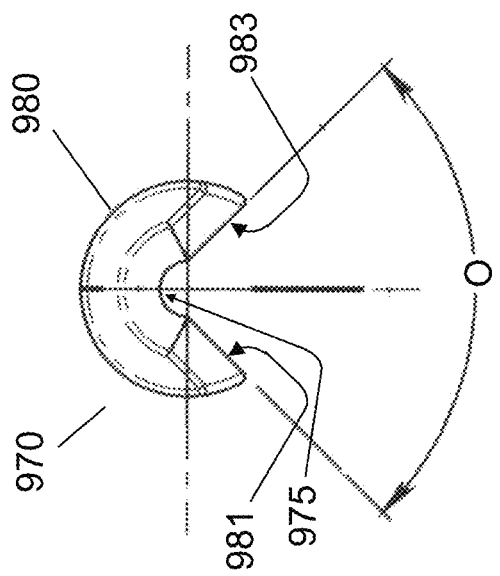

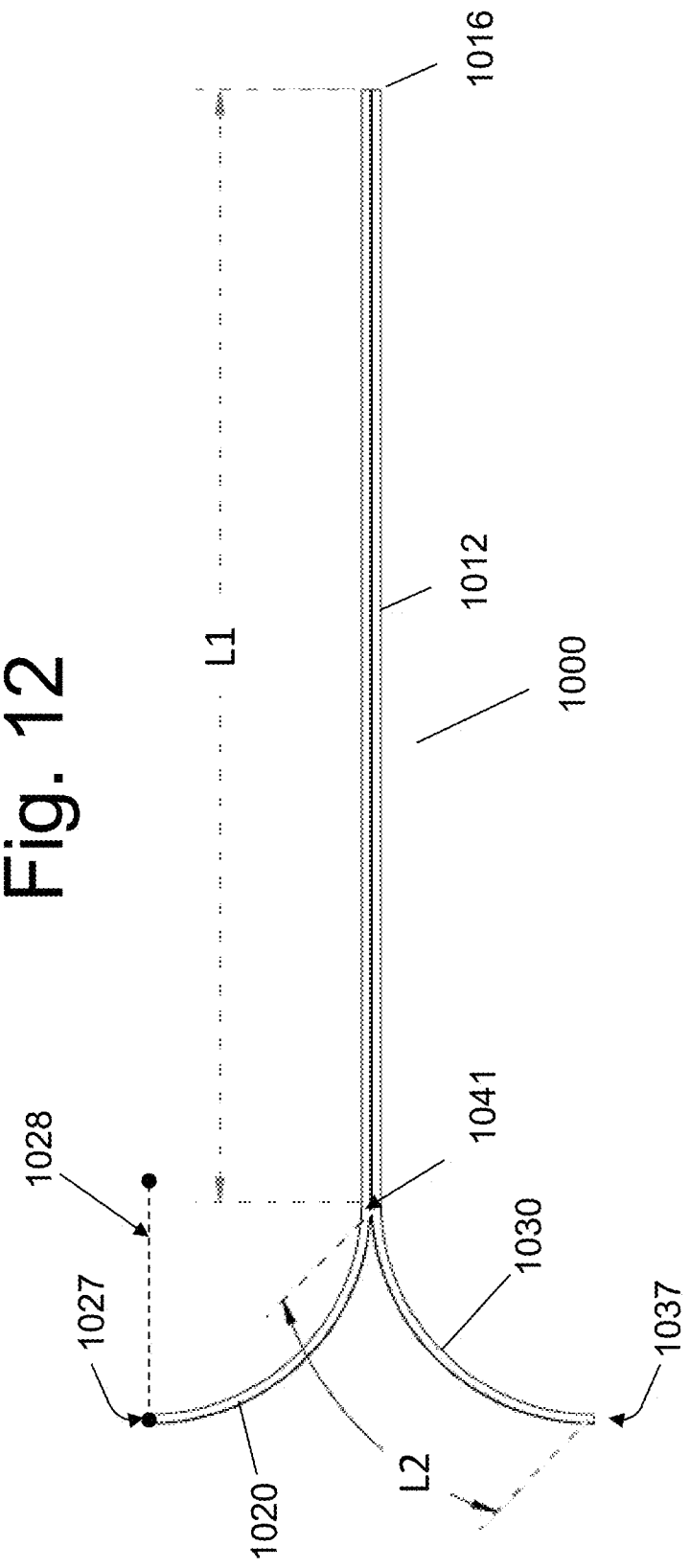

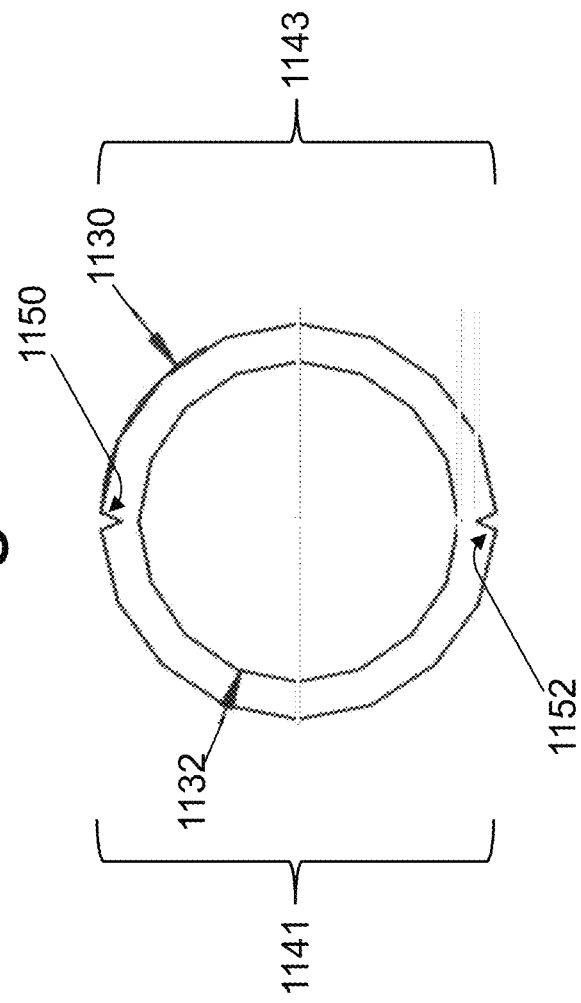

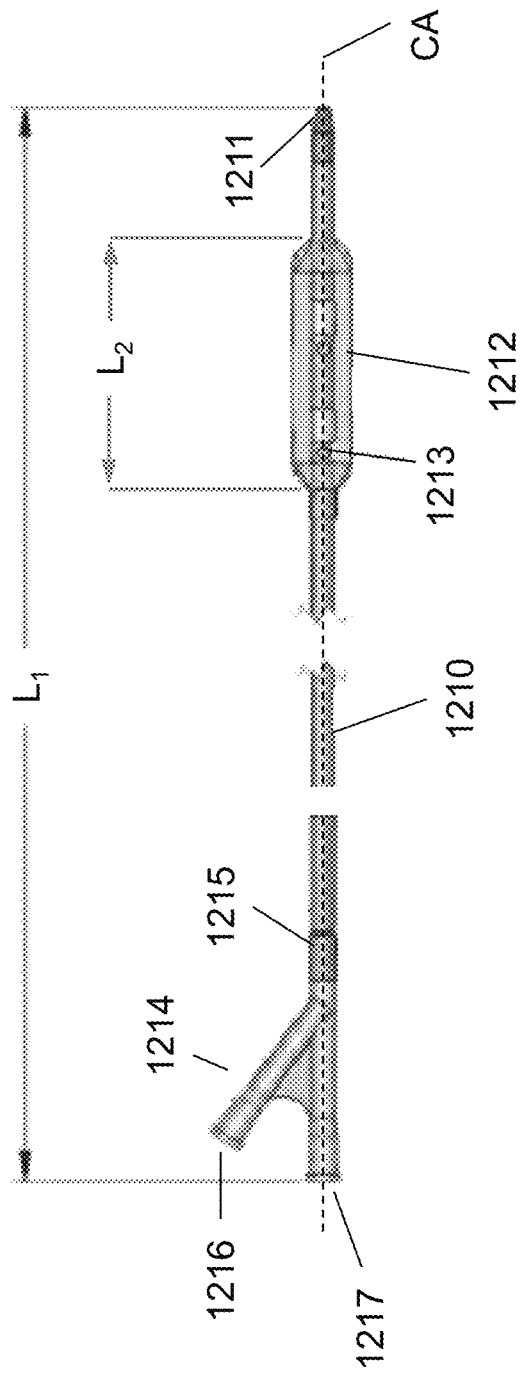

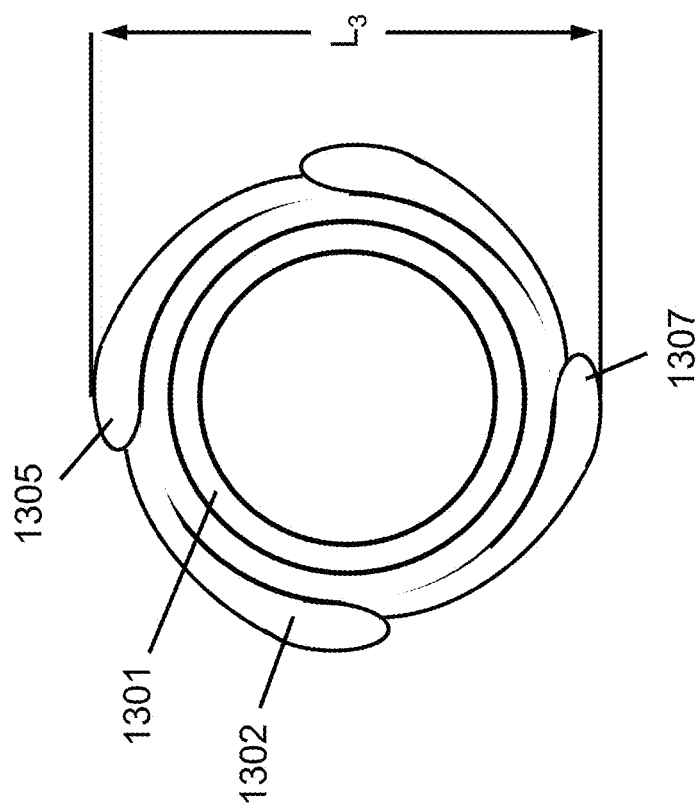

LUBRICIOUS INSERTION TOOLS FOR MEDICAL DEVICES AND METHODS FOR USING

CROSS-REFERENCE TO RELATED APPLICATIONS

The present non-provisional application claims the benefit of commonly owned provisional U.S. Application having Ser. No. 62/395,610, filed on Sep. 16, 2016, entitled LUBRICIOUS INSERTION TOOLS FOR MEDICAL DEVICES AND METHODS FOR USING, and commonly owned provisional U.S. Application having Ser. No. 62/464,520, filed on Feb. 28, 2017, entitled LUBRICIOUS INSERTION TOOLS FOR MEDICAL DEVICES AND METHODS FOR USING, which Applications are incorporated herein by reference in their entireties.

FIELD

The disclosure relates to insertion tools that facilitate the insertion of a medical device into the vasculature of the body.

BACKGROUND

Atherosclerosis is a disease that affects arteries of the body, with most cases affecting the coronary arteries. When occurring in arteries in the leg, either above or below the knee, the disease is often referred to as peripheral arterial disease (PAD). During the onset of atherosclerosis, changes in the walls of the arteries are seen characterized by increases in cholesterol content and scar tissue. Later on, atherosclerotic plaques build up and thicken the wall of the artery, forming lesions that often cause arterial narrowing or stenosis resulting in reduced a blood flow. At these later stages, calcium can be present in the plaques.

As a general matter, it is desired to treat patients found to have plaques because, whether the plaque impedes blood flow or not, their presence presents a risk of rupture which could trigger a coronary event. A ruptured plaque can stimulate local formation of a blood clot that can block the flow of blood. In coronary arteries this will cause myocardial infarction. In peripheral vessels this can cause severe pain and, if occurring in multiple vessels, may lead to critical limb ischemia.

SUMMARY

Described herein are insertion tools for medical devices that are introduced into the vasculature, and which can be used to treat arterial diseases such as atherosclerotic plaques. The insertion tools can be used for packaging and protecting an implantable or insertable medical device during storage and deployment. The insertion tools can also be used to protect and facilitate the insertion of a medical device such as a balloon catheter. The insertion tool may facilitate balloon catheter insertion through a hemostatic valve and into a patient catheter lumen, and can protect the surface of a balloon member of the balloon during loading. The insertion tool can also protect the device from contamination, and/or minimize or prevent loss of coating from the balloon catheter during insertion into the body.

Insertion tools of the present disclosure can also be used to protect health care professionals from having contact with drug coatings on medical devices that are inserted into the human body. Furthermore, the insertion tools can also act to protect humidity sensitive drug coatings and prevent accidental contact with fluids with the drug coatings prior to insertion into the body of a mammal.

The insertion tool can be a part of a kit or system used for a medical procedure, which are also embodiments of the invention. For example, the kit can include one or more of the following components: one or more delivery catheters, a balloon treatment device, an inflation catheter, a guidewire, a hemostatic valve, or combinations thereof.

In one embodiment, the invention provides an insertion tool configured to facilitate entry of a balloon portion of a balloon catheter into a patient's body through a hemostatic valve. The insertion tool includes: proximal and distal ends along a lengthwise axis; a tubular portion extending proximally from the distal end having a length that is least the length of the balloon portion length, and a tab at the proximal end. The tubular portion includes a wall, an inner diameter that can accommodates a balloon portion of a balloon catheter, a separation margin in the wall of a first lengthwise half of the tubular portion and which represents a structural weakening of, or a split in the wall in the first half. The tab at the proximal end is either (a) a tab that extends from a second lengthwise half of the tubular portion, the tab having a portion at an angle skew to the lengthwise axis, or a tab (b) in the form of a solid article comprising a concave surface that is fastened to an outer surface of the second lengthwise half of the tubular portion.

The invention also provides a balloon catheter insertion system comprising: (i) a balloon catheter comprising a balloon portion having a length, (ii) a hemostatic valve, and (iii) an insertion tool that facilitates entry of the balloon portion of the balloon catheter into a patient's body through the hemostatic valve, as described herein.

The invention also provides a method for inserting a balloon catheter in a patient's body. The method includes steps of: (a) providing a (i) a balloon catheter comprising balloon portion having a length and a catheter shaft proximal to the balloon portion (ii) an insertion tool to facilitate entry of the balloon catheter into a patient's body, the insertion tool as described herein; (b) inserting the distal end of the insertion tool in a hemostatic valve; (c) advancing the tubular portion of the insertion tool and balloon catheter therein through the hemostatic valve and into the patient's body; (d) withdrawing the tubular portion of the insertion tool from the hemostatic valve so as to position at least a proximal portion of the tubular portion around the catheter shaft; and (e) moving the insertion tool in relation to the balloon catheter to cause the separation margin to separate so the insertion tool can be moved away from the catheter shaft.

In another embodiment, the invention provides an insertion tool configured to facilitate entry of a balloon portion of a balloon catheter into a patient's body through a hemostatic valve, where the insertion tool includes proximal and distal ends along a lengthwise axis; a tubular portion extending proximally from the distal end having a length that is at least the length of the balloon portion length, the tubular portion including a wall, an inner diameter that can accommodate a balloon portion of a balloon catheter, first and second separation margins in the wall of the tubular portion representing structural weakenings of, or splits in the wall of the tubular portion, wherein the first and second separation margins define first and second lengthwise halves of the tubular portion; and a first tab that extends from the first lengthwise half of the tubular portion and a second tab that extends from the second lengthwise half of the tubular portion. The invention also provides a balloon catheter insertion system that includes this insertion tool, and also a method for inserting a balloon catheter in a patient's body, the method using this insertion tool or the system that includes the tool.

BRIEF DESCRIPTION OF THE DRAWINGS

FIG. 1 is an illustration of an insertion tool according to one embodiment of the disclosure.

FIG. 2 is an illustration of a portion of an insertion tool, as viewed from the distal end, according to one embodiment of the disclosure.

FIG. 3 is an illustration of a cross section of an insertion tool according to one embodiment of the disclosure.

FIG. 4 is an illustration of a distal end of an insertion tool according to one embodiment of the disclosure.

FIG. 5A is an illustration of a distal end of an insertion tool according to one embodiment of the disclosure.

FIG. 5B is an illustration of a cross section of a portion of a distal end of an insertion tool according to one embodiment of the disclosure.

FIG. 7 is an illustration of a proximal or distal end embodiment of an insertion tool.

FIG. 8 is an illustration of a proximal or distal end embodiment of an insertion tool.

FIG. 11 is an illustration of a portion of an insertion tool, as viewed from the proximal end, according to one embodiment of the disclosure.

FIG. 12 is an illustration of a perspective view of an insertion tool according to one embodiment of the disclosure.

FIG. 13 is an illustration of a distal end of an insertion tool according to one embodiment of the disclosure.

FIG. 14 is an illustration of portions of a balloon catheter, according to one embodiment of the disclosure.

FIG. 15 is an illustration of a distal end a balloon catheter showing a balloon portion in a folded configuration.

DESCRIPTION

Figure 6B:
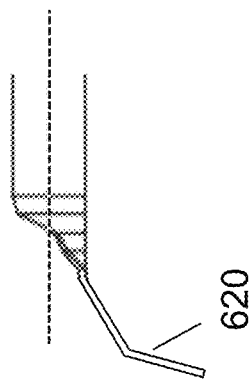
FIGS. 6A-6D are illustrations of proximal end embodiments of insertion tools.

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The terms "proximal" and "distal" are used herein to define the location of certain features of the balloon catheter insertion tool, or associated system components such as a balloon catheter or a hemostatic valve. The proximal end ("user end") refers to location of a feature of the system that is towards the user, i.e., towards the outside the body. The distal end ("treatment end") refers to location of a feature of the system that is away from the user end, i.e., towards the treatment site. A "proximal portion" refers to a portion that is more towards the proximal end relative to a portion that is more towards the distal end, which is a "distal portion." The "inner surface" ("luminal surface") refers to the surface of an article that is within the lumen of a hollow article, whereas the "outer surface" refers to the surface on the outside of the hollow article ("abluminal surface"). Likewise, the inner surface of such an article can define an "inner diameter," and the outer surface can define an "outer diameter," wherein the difference between the outer and inner diameters can define a "wall thickness," such as the thickness of the wall of the insertion tool. The arrangement of features of the insertion tool can also be explained with regards to a "lengthwise axis" of the tool which is a line including points at the proximal and distal ends of the tool and running parallel with the wall of the insertion tool.

With reference to FIG. 1, in one embodiment the disclosure provides a balloon catheter insertion tool 100 that includes a tubular portion 112 having proximal 114 and distal 116 ends. The tubular portion 112 has a lengthwise axis parallel with the wall of the tubular portion 112, and portions of the insertion tool may be described with regard to the relationship to the lengthwise axis. The tubular portion can have a length, i.e., the distance between the proximal 114 and distal 116 ends, which can accommodate the length of the balloon portion of a balloon catheter. The insertion tool can be used to house and facilitate insertion of balloon catheters of various shapes and sizes. For example, the length of the tubular portion can be at least about 10 mm, such as in the range of about 10 mm to about 300 mm; other exemplary ranges are in the range of about 10 mm to about 100 mm, about 50 mm to about 150 mm, and about 150 mm to about 300 mm.

FIG. 2 shows a view of the tubular portion of an insertion tool from its distal end 116. Although the tubular portion is shown as having a circular shape as viewed from the end, it can be of any shape (e.g., oval or polygonal) suitable for accommodating a balloon portion of a balloon catheter, and facilitating entry through a hemostatic valve.

FIG. 2 also shows the outer surface 130 and the inner surface of the 132 tubular portion. The distance between two points on the outer surface opposite each other, through the center of the tubular portion, represents the outer diameter (OD). The distance between two points on the inner surface opposite each other, through the center of the tubular portion, represents the inner diameter (ID). In exemplary embodiments the outer diameter of the tubular portion can be in the range of about 0.35 mm to about 10 mm, about 1.5 mm to about 5 mm, or about 1.6 mm to about 3 mm. In exemplary embodiments the circumference of the tubular portion can be in the range of about 1.1 mm to about 32 mm, about 2.5 mm to about 15 mm, or about 3 mm to 6 mm. In exemplary embodiments the inner diameter of the tubular portion can be in the range of 0.25 mm to 5 mm, about 1 mm to about 4 mm, about 1.2 mm to about 3 mm, or about 1.25 mm to about 2.75 mm. The lumen of the tubular portion can also be defined with regards to a cross-sectional area. Exemplary cross-sectional areas are in the range of about 0.05 mm² to about 20 mm², or about 0.75 mm² to about 12.5 mm².

The thickness of the wall of the tubular member can be determined by calculating half the difference of the outer diameter and the inner diameter. The wall thickness may be uniform around the circumference of the wall, or may be non-uniform. In exemplary embodiments the thickness of the wall of tubular portion can be about 0.025 mm or greater, about 0.05 mm or greater, about 0.075 mm or greater, or about 0.10 mm or greater, such as in the range of about 0.05 mm to about 2.5 mm, about 0.05 mm to about 0.5 mm, about 0.05 mm to about 0.25 mm, about 0.05 mm to about 0.20 mm, about 0.05 mm to about 0.15 mm, about 0.10 mm to about 0.25 mm, or about 0.15 mm to about 1.5 mm.

For purposes of explaining aspects of the disclosure, and with reference to FIG. 2, the tubular portion can be described as having a first lengthwise half 141, shown as the (upper) semi-circular half, and a second lengthwise half 143, shown as the (lower) semi-circular half. The first and second lengthwise halves are understood to extend between the proximal and distal ends running the length of the tubular portion. At least the first lengthwise half 141 can include a separation margin that can fracture when force is applied to the insertion tool (e.g., force applied to the tab of the tool, as discussed herein).

In one aspect, the separation margin can be in the form of a groove 150 (e.g., fissure, crevice, scored line, indentation) in the wall of the first lengthwise half 141. The groove 150 can be of any desired shape, such as V-shaped, U-shaped, rectangular or square shaped. A V-shaped groove 150 in the outer wall of the first lengthwise half 141 is shown in FIG. 2. The groove can be described in terms of its depth in the wall of the tubular portion. For example, in some embodiments the depth of the groove can be at least about 10% of the thickness of the wall where the groove is present. In some embodiments the depth of the groove can be in the range of about 10% to about 75% of the thickness of the wall, or about in the range of about 20% to about 60% of the thickness of the wall. Exemplary groove depths are in the range of about 0.025 mm to about 1 mm, about 0.05 mm to about 0.25 mm, or about 0.05 mm to about 0.15 mm. For example, for a wall thickness of about 0.5 mm, the groove may be a depth in the range of about 0.05 mm to about 0.375 mm, or for a wall thickness of about 0.075 mm, the groove may be a depth in the range of about 0.025 mm to about 0.070 mm. The desired depth of the groove can be determined by the wall thickness, the material used to make the tubular portion, the groove configuration, or combinations thereof.

In other aspects, the separation margin is a structural weakening in the wall of the tubular portion. The weakening can be due to a difference in the material of the tubular portion, or a difference in the physical property (e.g., molecular orientation) of the material at the separation margin as compared to another portion of the tubular member. Such a weakening can be introduced in the tubular member by a manufacturing process, such as extrusion processing. An extrusion process can induce a structural weakening along the separation margin by stretching the polymer composition used to make the tubular member. Stretching can be performed before extrusion, during extrusion, after extrusion, or combinations thereof. Stretching can induce coaxial alignment of the polymer molecules along the separation margin which can weaken the tubular member when force is applied in a direction perpendicular to the orientation of the polymer molecules.

The separation margin can be continuous along the first lengthwise half 141 (i.e., running from the proximal to distal end of the tubular portion), or non-continuous. If the separation margin is non-continuous along the first lengthwise half 141 it preferably includes few non-grooved interruptions to so the tubular member can still be separated in this half. Further, the separation margin can follow a linear path in the first lengthwise half 141, or alternatively can follow a non-linear path along the length (e.g., the separation margin can include one or more curves, angles, etc.)

In addition to the separation margin along the first lengthwise half 141, the tubular portion can optionally include one or more additional grooves in the first lengthwise half 141, the second lengthwise half 143, or both. If the tubular member includes one or more other (e.g., second, third, etc.) groove(s), the groove may or may not function as a separation margin. For example, the tubular portion may include a groove 152 in the second lengthwise half 143, such as one positioned geometrically opposite to the groove 150 in the first lengthwise half 141.

Upon application of force to the tubular member, groove 150 may fracture causing a split in the first lengthwise half 141 (e.g., due to force between the balloon catheter shaft and the inner surface of the tubular member adjacent to the groove 150). However, the same force may not cause any fracturing of the tubular wall adjacent to groove 152 (if such a groove is present), and therefore the second lengthwise half 143 may stay intact when the insertion tool is removed from the catheter shaft. Fabrication of the tubular member can be facilitated by forming pairs of grooves in the tubular member, with one groove geometrically opposite the other.

Referring now to FIG. 3, embodiments of the insertion tool include those wherein the proximal and/or distal ends of the tubular portion are flush, as well as those wherein the proximal and/or distal ends of the tubular portion are not flush. An insertion tool 200 with a flush (flat) distal end 216 of the tubular member 212. The end 214 of the tubular member 212 is shown having a tapered end, wherein tubular portion tapers from the first lengthwise half 241 to the second lengthwise half 243. Examples of non-flush configurations include tapered configurations and flared configurations. FIG. 4 illustrates an embodiment of an end of an insertion tool with a tapered configuration 316, which can be formed by cutting the distal end of a tubular article at an angle. An example of an end with a tapered and flared configuration 416 is shown in FIG. 5a, which is a top view of an end portion of an insertion tool showing the first lengthwise half 441 with separation margin 452, wherein the end 416 flares out. The flaring results in a widening of tubular portion at the end, as reflected by the increased width between points 425a and 425b as compared to the width (outer diameter) of the tubular portion that is adjacent to the end 416.

An insertion tool that includes a flared proximal opening can allow easier insertion of a balloon through the end, and can minimize or prevent the removal of therapeutic agent from the balloon surface, wherein the removal may be otherwise caused by frictional forces. Flaring the distal opening will allow to advance the tool over the balloon without scraping off drug.

Embodiments of the disclosure also include those wherein the wall of the tubular portion is tapered. For example, with reference to FIG. 5b, which shows a portion of a cross section of a tubular portion 455, the wall 460 at the end is tapered.

Embodiments of the disclosure include those wherein the insertion tool includes a tab at the proximal end of the tubular member, wherein the tab has a portion that extends from the second lengthwise half of the tubular portion, the tab portion at an angle skew to the lengthwise axis of the tubular portion. Examples of tabs having a portion that extends from the second lengthwise half of the tubular portion and skew to the lengthwise axis are shown in FIG. 1 (120), FIG. 3 (220), FIG. 6A (320), FIG. 6B (420), FIG. 6C (520), FIG. 6D (620), and FIG. 7 (720).

Figure 6A:
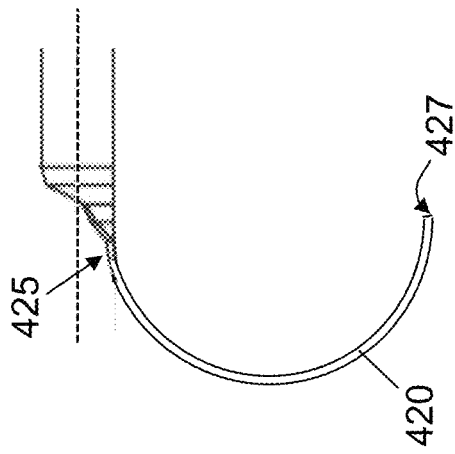

In embodiments, the tab can include curved shape, such as shown in FIGS. 1, 3, 6A, and 6B which are side views of proximal end portions of insertion tools. With reference to FIG. 6A, 321 points to a portion of the tab that is skew (dashed line SA representing the skew axis) to the lengthwise axis (dashed line LA) of the tubular member. It is understood that for a tab that include curved shape there can be multiple portions of the tab that are skew to the lengthwise axis of the tubular member.

A curved tab can be described various ways, such as by the length of the tab that follows the curvature. For example, this length can be represented in FIG. 3, from point 225 to 227; FIG. 6A, from point 325 to 327; and in FIG. 6B, from point 425 to 427. Exemplary tab lengths are in the range of about or about 5 mm to about 100 mm, or about 20 mm to about 40 mm.

A curved tab can also be described by the extent of its curve, expressed in degrees. For example, the curve of the tab in FIG. 3 is approximately 360°, whereas the curve of the tab in FIG. 6A is approximately 270°, and whereas the curve of the tab in FIG. 6B is approximately 180°. Exemplary curves are in the range of approximately 15° to approximately 540°, or approximately 30° to approximately 360°, or preferably approximately 45° to approximately 270°.

A curved tab can also described by its radius. For example, the radius of tab in FIG. 6A is represented by line 328. The radius of the curved tab may stay the same along the length of the tab, or can change. In some embodiments the radius of the tab can decrease, such as by up to about 50% of the starting radius (e.g., the radius adjacent or at point 235), or up to about 25% of the starting radius. Exemplary curved tab radii are in the range of about 1 mm to about 20 mm, or about 3 mm to about 10 mm.

Figure 6D:
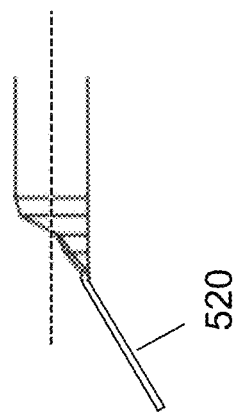
Figure 6C:
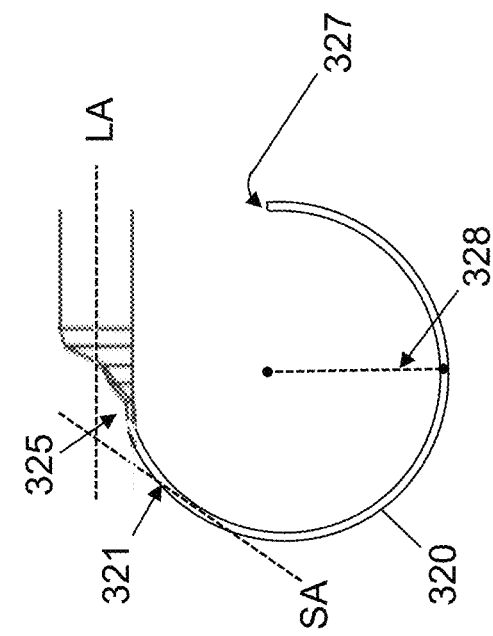

In embodiments of the disclosure as illustrated in FIGS. 6C and 6D, the tab (e.g., as viewed from a lengthwise cross-section of the insertion tool), can have one or more non-curved (e.g., straight) portions as represented by tab portions 520 and 620.

Embodiments of the disclosure include those wherein the tab has a second portion that extends from the second lengthwise half of the tubular portion, the second tab portion parallel the lengthwise axis of the tubular portion. FIG. 7 is an illustration of a tab that has a first portion 720 (i.e., a curved portion) that is at an angle skew to the lengthwise axis of the tubular portion, and a second portion 730 (i.e., a flat portion) that is parallel to the lengthwise axis of the tubular portion. Therefore, the second portion 730 will have a widthwise axis (e.g., dashed line 714) that is perpendicular to the lengthwise axis of the tubular member, and lengthwise axis that is parallel to the lengthwise axis of the tubular member, whereas the first portion 720 will have a widthwise axis that is perpendicular to the lengthwise axis of the tubular member, and lengthwise axis that is skew to the lengthwise axis of the tubular member.

Further, aspects of the tab immediately adjacent to the proximal end of the tubular portion can be described. For example, the tab can have a distal portion 725 that is curved (the distal portion extending from the curve of the second lengthwise half of the proximal end of the tubular portion). As the tab extends proximally, it can flatten (widthwise) from the curved shape. Also as the tab extends proximally the width of the tab can widen from a narrower width adjacent to the proximal end of the tubular member. Therefore the width of the tab can increase in a distal to a proximal direction. In exemplary embodiments, the width of the tab can be in the range of about 0.5 mm to about 30 mm, or about 2 mm to about 3.5 mm. A notch 735 can be present in the first lengthwise half of the tubular member, at the proximal end.

FIG. 8 is an illustration of another embodiment showing a tab having a first portion 750 (i.e., a curved portion) that can be at an angle skew to the lengthwise axis of the tubular portion, and a second portion 760 (i.e., a flat portion) that can be parallel to the lengthwise axis of the tubular portion. FIG. 8 also shows that between the proximal end 764 of the tubular portion and the second portion 760 (i.e., a flat portion) can be a tapered transition portion 765.

A tab that extends from the second lengthwise half of the tubular portion, and having a portion that can be at an angle skew to the lengthwise axis of the tubular portion can be formed by processing a flush end of a tubular member. For example, the following steps can be carried out to form a tab: (a) provide a tube having flush proximal and distal ends; (b) cut a slit partially through and perpendicular to the lengthwise axis of the tube to at least half the distance through the tube; (c) make a second cut into the tube between the proximal end and the slit, the cut made at an angle to meet the bottom of the slit cut (thereby forming a wedge-shaped cut in the upper half of the tube); force the cut proximal end downwards to flatten at least a portion of it (e.g., using heat forming).

In another embodiment, the insertion tool can include a split in the wall in the first half of the tubular portion. In this embodiment, during an insertion process the balloon catheter can be held within the inner diameter of a tubular member having such a configuration. After the insertion tool facilitates the insertion of the balloon catheter through the hemostatic valve, the tubular portion can be moved proximally so the tubular portion surrounds a portion of the balloon catheter shaft. Force can be then be applied to the tab so the first half of the tubular portion opens to the movement of the catheter shaft out of the inner diameter of the tubular portion. In particular, the force applied to the tab can cause the walls of the tubular portion on either side of the split to move apart, thereby providing a lengthwise gap that the catheter shaft can be moved through.

Figure 9:
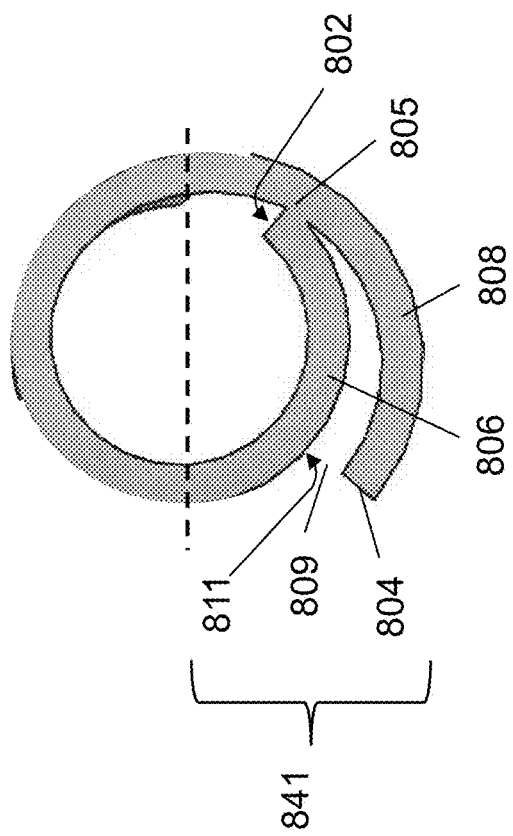
FIG. 9 is an illustration of a portion of an insertion tool, as viewed from the distal end, according to one embodiment of the disclosure.

An exemplary embodiment of an insertion tool having a split in the wall in the first half of the tubular portion 841 is shown in FIG. 9, which is a cross section view of the tubular portion from the distal end. The split in first half of the wall can provide first edge 802 and second edge 804, which extend the length of the tubular portion. A point on the outer wall adjacent to first edge 802 and can contact a point 805 on the inner wall of tubular member in first half. As such, as viewed from the proximal end, the first half can include an inner overlapping portion of the wall 806, and an outer overlapping portion of the wall 808.

The circumferential distance between the first edge 802 and point 805 can form an inner diameter large enough to accommodate a balloon catheter of choice. For example, in these embodiments, the outer diameter of the tubular portion can be in the range of about 0.45 mm to about 10 mm, or about 1.5 mm to about 5 mm, and the inner diameter of the tubular portion can be in the range of 0.25 mm to 5 mm, or about 1 mm to about 4 mm. The dimensions/length of the outer overlapping portion of the wall 808 (between edge 804 and point 805) can be described, such as in relation to other portions of the insertion tool. For example, the length (804-805) can be less than the circumference 802-805, or a length in the range of about 5% to about half of the circumference (about 5% to 50% of 802-805).

There also may be a gap 809 between the inner surface of the outer overlapping portion of the wall 808 (i.e., adjacent edge 804) and the adjacent point 811 of the outer surface of the inner overlapping portion of the wall 806. The gap 809 can be a distance in the range of a fraction of the wall thickness to many times the wall thickness, for example in the range of about 0 mm (no gap) to about 0.5 mm.

Figure 10:
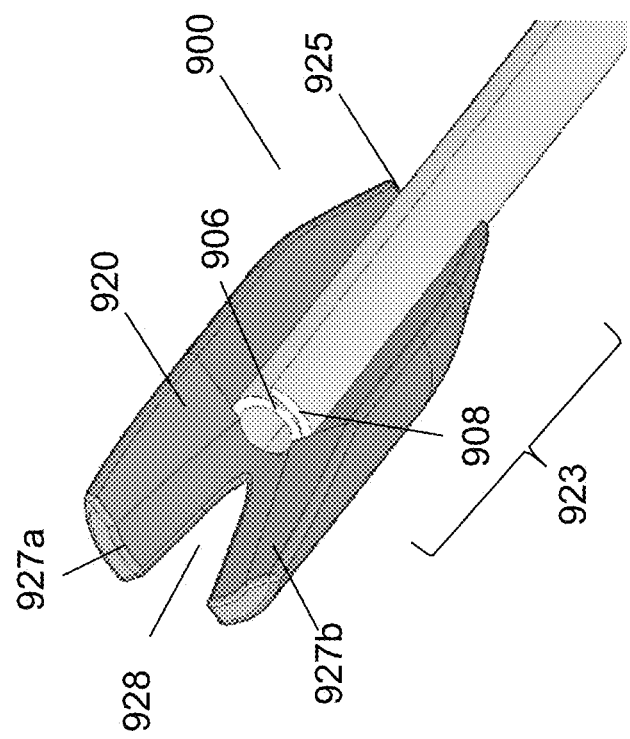
FIG. 10 is an illustration of a portion of an insertion tool, as viewed from the proximal end, according to one embodiment of the disclosure.

FIG. 10 is a perspective view of the proximal portion of an insertion tool 900 having a split in the wall in the first half of the tubular portion, and a tab at the proximal end in the form of a solid article tab 920 comprising a concave surface that is attached (e.g., fastened or fixed) to an outer surface of the second lengthwise half of the tubular portion. Shown from the first half of the tubular portion are the inner overlapping portion of the wall 906, and the outer overlapping portion of the wall 908. The distance from the proximal end of the tubular portion to the distal end of the tab 925 (i.e., attachment length 923) can be in the range of about 5 mm to about 25 mm. The tab 920 can include two or more proximal extension portions, for example proximal extension portions 927a and 927b, which can have a relatively flat shape. The extension portions can narrow from near the center of the tab to the proximal end of the tab (i.e., in a lengthwise direction). Further, the extension portions can have a thickness (i.e., in a radial direction) that is greater near the center of the tab than their thickness at the proximal end of the tab.

FIG. 11 is a cross section that shows an embodiment of the solid article tab 970 with concave surface that can be fastened to an outer surface of the second lengthwise half of the tubular portion as viewed from its proximal end. Concave surface 975 of tab 970 is shown, and this surface can have a semicircular shape with an inner diameter that corresponds to the outer diameter of the second half of the proximal end of the tubular portion. The outer diameter of the second half of the proximal end of the tubular portion can be attached to the concave surface 975 of tab 970 though a suitable attachment material or member, such as an adhesive.

FIG. 11 also shows that the outer surface 980 of the tab 970 can be curved (e.g., having a partially circular shape) as viewed from its proximal end. The outer surface can extend a desired distance as defined by degrees, such as a distance in the range of about 45° to about 300°, or about 180° to about 270°, such as measured between surfaces 981 and 983. The opening O, or gap, between surfaces 981 and 983, can also be defined, and can be in the range of about 60° to about 315°, or about 90° to about 180°. The solid article tab (e.g., 920, 970) can also be defined by a thickness between its inner and outer surfaces (e.g., between concave surface 975 and outer surface 980), with an exemplary thickness in the range of about 0.5 mm to about 5 mm, or about 1 mm to about 2 mm. In one mode of fabrication, an adhesive is applied between concave surface 975 and the outer surface of the second lengthwise half of the tubular portion (i.e., opposite the first lengthwise half including the split in the wall) in order to attach the solid article tab 970 to the tubular portion.

Referring to FIG. 12, another embodiment of the insertion tool includes two curved tabs at the proximal end of the insertion tool. The insertion tool 1000 is shown with a flush (flat) distal end 1016 of the tubular portion 1012. Alternatively, the distal end can be tapered, such as according to a tapered configuration of other tool embodiments of the disclosure. The tubular portion 1012 can extend a predetermined distance (L1) from the distal end 1016 to a point 1041 where tabs 1020 and 1030 begin. Point 1041 can be a location of a split in the tubular member. At point 1041 one half of the tubular member can form a first tab 1020, and the other half of the tubular member can form a second tab 1030. Tabs 1020 and 1030, as shown in the figure, can be curved. Tabs 1020 and 1030 can terminate at proximal ends 1027 and 1037, respectively.

Tabs 1020 and 1030 can follow any curved path, such as a circular or an elliptical path. Tabs 1020 and 1030 can also be described by the extent of its curve, expressed in degrees. For example, the curve of Tabs 1020 and 1030 in FIG. 12 is approximately 90°, and exemplary tabs are in the range of approximately 45° to approximately 270°, or approximately 45° to approximately 180°. The curved tabs 1020 and 1030 can also described by their radii. For example, the radius of tab 1020 is represented by line 1028. The radius of tab 1020 can be the same or different than tab 1030. The radius of the curved tab may stay the same along the length of the tab, or can change. In this embodiment, exemplary curved tab radii are in the range of about 5 mm to about 35 mm, or about 10 mm to about 30 mm.

The insertion tool 1000 can also be described in terms of the length of the tubular portion 1012 and one or both tabs 1020 and 1030. In embodiments, the length L1 of the tubular portion 1012 is greater than the length L2 one or both tabs 1020 and 1030, and preferably the length L1 of the tubular portion 1012 is two or more times, or three or more times greater than the length L2 one or both tabs 1020 and 1030. In exemplary the length L1 of the tubular portion 1012 is in the range of about 25 mm to about 150 mm, or about 75 mm to about 125 mm.

The insertion tool 1000 of FIG. 12 can be prepared using a tubular portion having a configuration according to FIG. 13 (wherein the tubular portion is similar to, or the same as, the one shown in FIG. 2), which illustrates the tubular portion as viewed from the distal end. The tubular portion can have a first lengthwise half 1141 as the (left) semi-circular half, and a second lengthwise half 1143 as the (right) semi-circular half. The first and second lengthwise halves are understood to extend between the proximal and distal ends running the length of the tubular portion 1012. The first and second lengthwise halves are defined by first separation margin 1150 (e.g., a V-shaped groove) and second separation margin 1152 (e.g., another V-shaped groove). Tabs 1020 and 1030 are formed as extensions of the first lengthwise half 1141 and second lengthwise half 1143 which are split at point 1041 and configured to angle away (e.g., as in a curved arrangement as shown) from the central axis of the tubular portion 1012. FIG. 13 also shows the outer surface 1130 and the inner surface of the 1132 tubular portion.

In some embodiments of the insertion tool the first separation margin 1150 and the second separation margin 1152 can be structural weakenings in the tubular portion 1012, the weakenings representing a difference in the material of the tubular portion, or a difference in the physical property (e.g., molecular orientation) of the material at the separation margins. In some embodiments, the weakening can be introduced in the tubular member by the process of manufacture. As a non-limiting example, a structural weakening in the tubular portion can be intentionally induced through extrusion processing. An extrusion process can induce a structural weakening along the separation margin by stretching the polymer composition used to make the tubular member. Stretching can be performed before extrusion, during extrusion, after extrusion, or combinations thereof. Stretching can induce coaxial alignment of the polymer molecules along the separation margin which can weaken the tubular member when force is applied in a direction perpendicular to the orientation of the polymer molecules. This also can create a natural split at point 1041.

Force can be applied to the insertion tool 1000 to cause separation of the first and second lengthwise halves (1141 and 1143). For example, a user can pull tabs 1020 and 1030 outwardly, away from the central axis of the tubular portion 1012. This in turn can cause the tubular portion 1012 to fracture along first and second separation margins (1150 and 1152).

The embodiment of FIG. 12 can include any dimension of overall length, outer diameter, inner diameter, or wall thickness as described herein; can include any tube configuration including distal end configuration as described herein; can be formed from any material or by any process as described herein; and can be used with any balloon catheter or hemostatic valve as described herein, or known in the art.

The tubular portion, tab, or both, can be formed by techniques such as extrusion, 3D printing, injection molding, compression molding, particulate leaching, solvent casting, thermoforming, or cutting. A combination of fabrication techniques can be used. Features of the insertion tool (e.g., separation margin, tab) can be formed during extrusion, molding, etc., or afterwards. Exemplary materials that can be used to fabricate a part of, or all of, the insertion tool include polymer-based materials such as fluorinated ethylene propylene (FEP); low and high density polyethylene (HDPE and LDPE), polytetrafluoroethylene (PTFE; Teflon); polyurethane; PEBAX, polyesteramide, polyimide, polyester, and polyamide (Nylon).

The material used to make portions of the insertion tool, such as the tubular portion, thereof can be transparent and able to transmit UV light. Various aliphatic polymers, including halogenated aliphatic polymers can provide good transmission of UV light. In some embodiments, a coating composition including a UV-activated crosslinker as described herein can be applied to the inner surface (inner diameter) of the tubular member of the insertion tool, and the tubular member can be irradiated with UV light which traverses the material of the tubular member and activates the crosslinker to form a durable coating.

All or part of the insertion tool can be fabricated to provide a visual or detectable distinction between the insertion tool and another part of the balloon catheter insertion system, such as the balloon catheter and/or the hemostatic valve. Components of the balloon catheter insertion system may be fabricated from similar materials, and therefore portions of the system components may be otherwise difficult to distinguish from each other when they are used together if a detection material is not used with one or more components of the system. For example, the detection material can be a colorant, material which reflects light (e.g., to increase the opacity of the insertion tool), a radioopaque material, a paramagnetic material, a vapor phase material, or a radioisotopic materials.

For example, a colorant or imaging agent can be provided at one or more portions along the length of the insertion tool and/or balloon catheter. The colorant or imaging agent can facilitate monitoring of the progress of insertion of the balloon catheter into a patient. The colorant(s) or imaging agent can provide a visual cue to the practitioner that indicates the spatial relationship of a part of the insertion tool with a part of the balloon catheter. Being able to visually determine the portions of the device can improve the insertion process.

A colorant or imaging agent can be used on or in a polymeric material used that is used to fabricate the insertion tool and/or balloon catheter. A colorant can also be used in a lubricious coating material (such as a polymeric hydrogel coating) that is optionally applied to a surface of insertion tool and/or balloon catheter.

Example of colorants include, but are not limited to, FD&C and D&C lakes, titanium dioxide, magnesium carbonate, talc, pyrogenic silica, iron oxides, channel black, insoluble dyes, natural colorants (such as riboflavin, carmine 40, curcumin, and annatto), dyes approved for ingestion by the U.S. Federal Drug Administration, or a combination of any of these. Colorants used in making coating dispersions for coating tablets, food, confectionery forms, agricultural seeds, and the like can be used in association with articles of the current disclosure.

Figure 17:
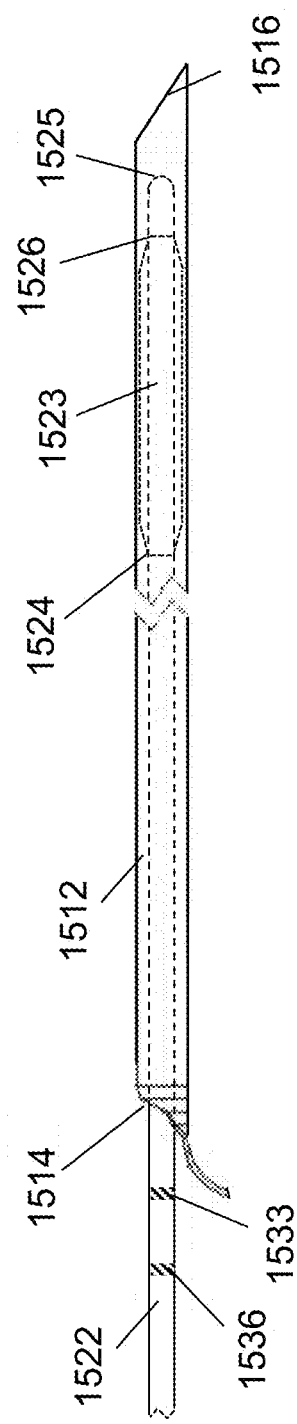
FIG. 17 is an illustration of a portion of a balloon catheter within an insertion tool.

A colorant or imaging agent can be present on one or more portions of the insertion tool, the balloon catheter, or any other component that may be used in conjunction with the tool and catheter, in order to facilitate entry of the catheter into the body. For example, with reference to FIG. 17, balloon portion 1523 is shown located within the tubular portion 1512 of an insertion tool. A first catheter marking 1536 and second catheter making 1533 can be located at points along the length of the catheter body 1522, and visible to a user during the insertion process. Markings along the catheter body can positionally correspond to portion(s) of the catheter (e.g., points along the balloon portion 1523), which may not be visible to the user. For example, the distance between second catheter making 1533 and the proximal end of the insertion tool 1514 can correspond to the distance between the distal tip of the balloon catheter 1525 and the distal end of the insertion tool 1516. Monitoring the position of the second catheter making 1533 relative to the proximal end of the insertion tool 1514 can allow the user to understand when the distal tip 1525 emerges from the distal end 1516 during an insertion process. Likewise, the distance between the first catheter marking 1536 and the distal end 1516 (or the second catheter making 1533) can allow the user to understand the location of the distal end of the balloon portion 1526 during insertion of the balloon catheter.

Figure 18:
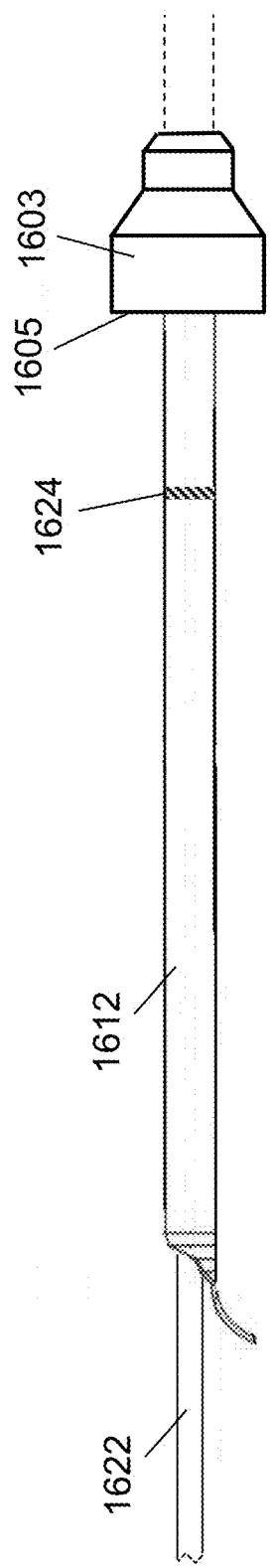
FIG. 18 is an illustration of a portion of a balloon catheter within an insertion tool, and a portion of the insertion tool within a hemostatic valve.

With reference to FIG. 18, markings can also be present on the outer surface of the tubular member of the insertion tool 1612 and can be helpful for understanding the positioning of the distal end of the insertion tool (not shown) relative to portions of a hemostatic valve 1603 which the insertion tool 1612 is being passed through. For example, in use, the insertion tool 1612 through hemostatic valve 1603 to marking 1624, which can indicate the distal end of the insertion tool has reached the distal end of the hemostatic valve. Following this, the body of the balloon catheter 1622 can be advanced to move the balloon catheter into the patient.

Alternatively, or in addition to the insertion tool marking, the tubular member of the insertion tool can include a stop member (not shown) that extends radially outwards from its surface, that meets a portion of the proximal end 1605 of the hemostatic valve, and which effectively prevents further distal movement of the insertion tool through the hemostatic valve. The stop member may be in the form of a raised circumferential lip or bulge from the outer surface of the tubular member, or any other structure that is able to contact the proximal portion of the hemostatic valve. The stop member can be formed as part of an extrusion process used to make the insertion tool, or can be added to the tubular member after it is formed, for example by adhering a plastic ring to a desired location on the outer surface of the tubular member.

In embodiments of the disclosure, any portion of any insertion tool/article, or any portions of catheter of the disclosure can have a coating, such as a hydrophilic lubricious coating. For example, hydrophilic polymeric base coatings can be applied to portions of the insertion tool/article, or any portions of catheter to impart lubricity and decrease loss of desired material (e.g., therapeutic agent from the balloon surface). In other embodiments, any portion of any insertion tool/article, or any portions of catheter of the disclosure can be associated with a low friction article such as a Teflon sleeve. In some embodiments, all or a portion of the inner diameter of the tubular member of the insertion tool is coated with a hydrophilic coating, or lined with lubricious low friction sleeve (e.g. PTFE and PTFE liners). In some embodiments, all or a portion of the outer surface of the balloon catheter is coated with a hydrophilic coating, or lined with lubricious low friction sleeve. Other materials for providing a lubricious low friction coating includes silicone oil, perfluorinated oils and waxes, optionally with covalently bonding, which imparts lower friction.

One class of hydrophilic polymers useful as polymeric materials for hydrophilic base coat formation can be synthetic hydrophilic polymers. Synthetic hydrophilic polymers that are biostable (i.e., that show no appreciable degradation in vivo) can be prepared from any suitable monomer including acrylic monomers, vinyl monomers, ether monomers, or combinations of any one or more of these types of monomers. Acrylic monomers include, for example, methacrylate, methyl methacrylate, hydroxyethyl methacrylate, hydroxyethyl acrylate, methacrylic acid, acrylic acid, glycerol acrylate, glycerol methacrylate, acrylamide, methacrylamide, dimethylacrylamide (DMA), and derivatives and/or mixtures of any of these. Vinyl monomers include, for example, vinyl acetate, vinylpyrrolidone, vinyl alcohol, and derivatives of any of these. Ether monomers include, for example, ethylene oxide, propylene oxide, butylene oxide, and derivatives of any of these. Examples of polymers that can be formed from these monomers include poly(acrylamide), poly(methacrylamide), poly(vinylpyrrolidone), poly(acrylic acid), poly(ethylene glycol), poly(vinyl alcohol), and poly (HEMA). Examples of hydrophilic copolymers include, for example, methyl vinyl ether/maleic anhydride copolymers and vinyl pyrrolidone/(meth)acrylamide copolymers. Mixtures of homopolymers and/or copolymers can be used.

Examples of some acrylamide-based polymers, such as poly(N,N-dimethylacrylamide-co-aminopropylmethacrylamide) and poly(acrylamide-co-N,N-dimethylaminopropyl-meth-acrylamide) are described in example 2 of U.S. Pat. No. 7,807,750 (Taton et al.), the disclosure of which is incorporated herein by reference.

Other hydrophilic polymers that can be useful in the present disclosure are derivatives of acrylamide polymers with photoreactive groups. One such representative hydrophilic polymer can be the copolymerization of N-[3-(4-benzoylbenzamido)propyl]methacrylamide (Formula I) with N-(3-aminopropyl)methacrylamide (Formula II) to produce the polymer poly(N-3-aminopropyl)methacrylamide-co-N-[3-(4-benzoylbenzamido)propyl]methacrylamide (Formula III). The preparation of the polymer is disclosed in Example 1 of US Patent Publication 2007/0032882 (to Lodhi, et al.), the full content of which is incorporated herein by reference.

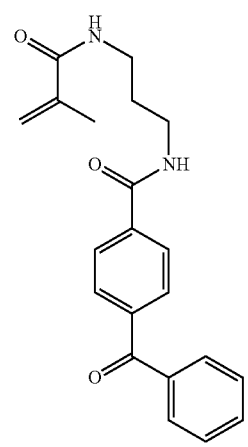

Formula I

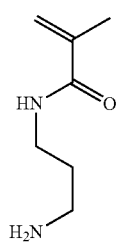

Formula II

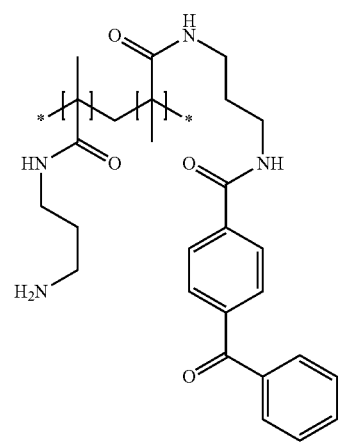

Formula III

In some embodiments, the hydrophilic polymer can be a vinyl pyrrolidone polymer, or a vinyl pyrrolidone/(meth) acrylamide copolymer such as poly(vinylpyrrolidone-co-methacrylamide). If a PVP copolymer is used, it can be a copolymer of vinylpyrrolidone and a monomer selected from the group of acrylamide monomers. Exemplary acrylamide monomers include (meth)acrylamide and (meth) acrylamide derivatives, such as alkyl(meth)acrylamide, as exemplified by dimethylacrylamide, and aminoalkyl(meth) acrylamide, as exemplified by aminopropylmethacrylamide and dimethylaminopropylmethacrylamide. For example, poly(vinylpyrrolidone-co-N,N-dimethylaminopropylmeth-acrylamide) is described in example 2 of U.S. Pat. No. 7,807,750 (Taton et al.).

In one embodiment, the polymers and copolymers as described are derivatized with one or more photoactivatable group(s). Exemplary photoreactive groups that can be pendent from biostable hydrophilic polymer include aryl ketones, such as acetophenone, benzophenone, anthraquinone, anthrone, quinone, and anthrone-like heterocycles.

Aryl ketones herein can specifically include diaryl ketones. Polymers herein can provide a hydrophilic polymer having a pendent activatable photogroup that can be applied to the expandable and collapsible structure, and can then treated with actinic radiation sufficient to activate the photogroups and cause covalent bonding to a target, such as the material of the expandable and collapsible structure. Use of photo-hydrophilic polymers can be used to provide a durable coating of a flexible hydrogel matrix, with the hydrophilic polymeric materials covalently bonded to the material of the expandable and collapsible structure.

A hydrophilic polymer having pendent photoreactive groups can be used to prepare the flexible hydrogel coating. Methods of preparing hydrophilic polymers having photoreactive groups are known in the art. For example, methods for the preparation of photo-PVP are described in U.S. Pat. No. 5,414,075 (to Swan et al.), the disclosure of which is incorporated herein by reference. Hydrophilic photo-polyacrylamide polymers such as poly(acrylamide-co-N-(3-(4-benzoylbenzamido)propyl) methacylamide)"Photo PA," and derivatives thereof can be used to form hydrophilic base coats on articles in exemplary embodiments of the present disclosure. Methods for the preparation of photo-polyacrylamide are described in U.S. Pat. No. 6,007,833 (to Chudzik et al.), the disclosure of which is incorporated herein by reference.

Other embodiments of hydrophilic base coats include derivatives of photo-polyacrylamide polymers incorporating additional reactive moieties. Some exemplary reactive moieties include N-oxysuccinimide and glycidyl methacrylate. Representative photo-polyacrylamide derivatives incorporating additional reactive moieties include poly(acrylamide-co-maleic-6-aminocaproic acid-N-oxysuccinimide-co-N-(3-(4-benzoylbenzamido)propyl) methacrylamide) and poly(acrylamide-co-(3-(4-benzoylbenzamido)propyl) methacrylamide)-co-glycidylmethacrylate. Additional photo-polyacrylamide polymers incorporating reactive moieties are described in U.S. Pat. No. 6,465,178 (to Chappa, et al.), U.S. Pat. No. 6,762,019 (to Swan, et al.) and U.S. Pat. No. 7,309,593 (to Ofstead, et al.), the disclosures of which are herein incorporated by reference.

Other embodiments of exemplary hydrophilic base coats that include derivatives of photo-polyacrylamide polymers incorporating additional reactive moieties can be found in U.S. Pat. No. 6,514,734 (to Clapper, et al.), the disclosure of which is incorporated herein by reference in its entirety.

In yet other embodiments, the hydrophilic base coat can include derivatives of photo-polyacrylamide polymers incorporating charged moieties. Charged moieties include both positively and negatively charged species. Exemplary charged species include, but are not limited to, sulfonates, phosphates and quaternary amine derivatives. Some examples include the negatively charged species N-acetylated poly(acrylamide-co-sodium-2-acrylamido-2-methyl-propanesulfonate-co-N-(3-(4-benzoylbenzamido)propyl) methacrylamide)-co-methoxy poly(ethylene glycol) monomethacrylate. Other negatively charged species that can be incorporated into the hydrophilic base coat are described in U.S. Pat. No. 4,973,493 (to Guire et al.), the disclosure of which is incorporated herein by reference in its entirety. Positively charged species can include poly(acrylamide-co-N-(3-(4-benzoylbenzamido) propyl)methacrylamide)-co-(3-(methacryloylamino)propyl)trimethylammonium chloride. Other positively charged species that can be incorporated into a hydrophilic base coat are described in U.S. Pat. No. 5,858,653 (to Duran et al.), the disclosure of which is incorporated herein by reference in its entirety.

In another embodiment, the polymers and copolymers as described are derivatized with one or more polymerizable group(s). Polymers with pendent polymerizable groups are commonly referred to as macromers. The polymerizable group(s) can be present at the terminal portions (ends) of the polymeric strand or can be present along the length of the polymer. In one embodiment polymerizable groups are located randomly along the length of the polymer.

Exemplary hydrophilic polymer coatings can be prepared using polymer grafting techniques. Polymer grafting techniques can include applying a nonpolymeric grafting agent and monomers to a substrate surface then causing polymerization of the monomers on the substrate surface upon appropriate activation (for example, but not limited to, UV radiation) of the grafting agent. Grafting methods producing hydrophilic polymeric surfaces are exemplified in U.S. Pat. Nos. 7,348,055; 7,736,689 and 8,039,524 (all to Chappa et al.) the full disclosures of which are incorporated herein by reference.

Alternatively, a coating composition can include thermally-reactive polymers (e.g., a hydrophilic polymer with pendent thermally reactive peroxide groups), such as described in U.S. Pat. No. 7,807,750 (Taton et al.). In exemplary embodiments a coating composition with a thermally reactive polymer is applied to the inner surface of the tubular member (inner diameter) and heated to cause chemical reaction of the activated pendent groups to the material of the tubular member and bonding of the polymer.

Optionally, a coating on an article of the current disclosure can include a crosslinking agent. A crosslinking agent can promote the association of polymers in a coating, or the bonding of polymers to a coated surface. The choice of a particular crosslinking agent can depend on the ingredients of the coating composition.

Suitable crosslinking agents can include two or more activatable groups, which can react with the polymers in the composition. Suitable activatable groups can include photoreactive groups as described herein, like aryl ketones, such as acetophenone, benzophenone, anthraquinone, anthrone, quinone, and anthrone-like heterocycles. A crosslinking agent including a photoreactive group can be referred to as a photo-crosslinker or photoactivatable crosslinking agent. The photoactivatable crosslinking agent can be ionic, and can have good solubility in an aqueous composition. Thus, in some embodiments, at least one ionic photoactivatable crosslinking agent can be used to form a coating. The ionic crosslinking agent can include an acidic group or salt thereof, such as selected from sulfonic acids, carboxylic acids, phosphonic acids, salts thereof, and the like. Exemplary counter ions include alkali, alkaline earths metals, ammonium, protonated amines, and the like.

Exemplary ionic photoactivatable crosslinking agents include 4,5-bis(4-benzoylphenyl-methyleneoxy) benzene-1,3-disulfonic acid or salt; 2,5-bis(4-benzoylphenylmethyleneoxy) benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,077,698 (Swan et al.), U.S. Pat. No. 6,278,018 (Swan), U.S. Pat. No. 6,603,040 (Swan) and U.S. Pat. No. 7,138,541 (Swan) the disclosures of which are incorporated herein by reference.

Other exemplary ionic photoactivatable crosslinking agents include ethylenebis(4-benzoylbenzyldimethylammonium) dibromide and hexamethylenebis(4-benzoylbenzyl dimethylammonium) dibromide and the like. See U.S. Pat. No. 5,714,360 (Swan et al.) the disclosures of which are incorporated herein by reference.

In yet other embodiments, restrained multifunctional reagents with photoactivable crosslinking groups can be used. In some examples these restrained multifunctional reagents include tetrakis (4-benzoylbenzyl ether) of pentaerthyritol and the tetrakis (4-benzoylbenzoate ester) of pentaerthyritol. See U.S. Pat. No. 5,414,075 (Swan et al.) and U.S. Pat. No. 5,637,460 (Swan et al.) the disclosures of which are incorporated herein by reference.

Additional crosslinking agents can include those having formula Photo1-LG-Photo2, wherein Photo1 and Photo2 independently represent at least one photoreactive group and LG represents a linking group comprising at least one silicon or at least one phosphorus atom, wherein the degradable linking agent comprises a covalent linkage between at least one photoreactive group and the linking group, wherein the covalent linkage between at least one photoreactive group and the linking group is interrupted by at least one heteroatom. See U.S. Pat. No. 8,889,760 (Kurdyumov, et al.), the disclosure of which is incorporated herein by reference. Further crosslinking agents can include those having a core molecule with one or more charged groups and one or more photoreactive groups covalently attached to the core molecule by one or more degradable linkers. See U.S. Publ. Pat. App. No. 2011/0144373 (Swan, et al.), the disclosure of which is incorporated herein by reference.

In some embodiments, the first and/or second crosslinking agent can have a molecular weight of less than about 1500 kDa. In some embodiments the crosslinking agent can have a molecular weight of less than about 1200, 1100, 1000, 900, 800, 700, 600, 500, or 400.

In some embodiments, at least one of the first and second crosslinking agents comprising a linking agent having formula Photo1-LG-Photo2, wherein Photo1 and Photo2, independently represent at least one photoreactive group and LG represents a linking group comprising at least one silicon or at least one phosphorus atom, there is a covalent linkage between at least one photoreactive group and the linking group, wherein the covalent linkage between at least one photoreactive group and the linking group is interrupted by at least one heteroatom.

In some embodiments, at least one of the first and second crosslinking agents comprising a linking agent having a formula selected from:

(a)
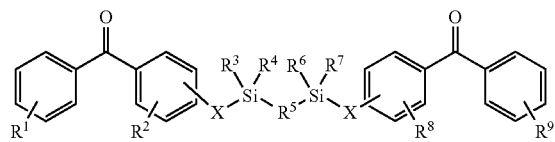

wherein R1, R2, R8 and R9 are any substitution; R3, R4, R6 and R7 are alkyl, aryl, or a combination thereof; R5 is any substitution; and each X, independently, is O, N, Se, S, or alkyl, or a combination thereof;

(b)
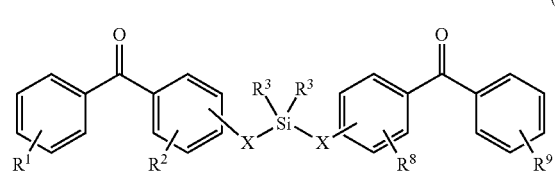

wherein R1 and R5 are any substitution; R2 and R4 can be any substitution, except OH; R3 can be alkyl, aryl, or a combination thereof; and X, independently, are O, N, Se, S, alkylene, or a combination thereof;

(c)
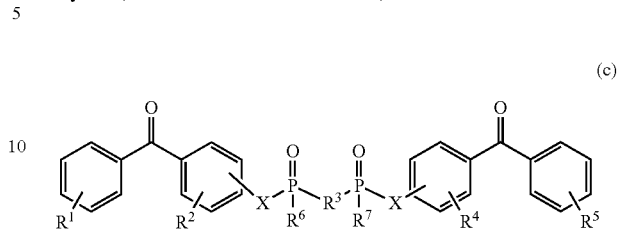

wherein R1, R2, R4 and R5 are any substitution; R3 is any substitution; R6 and R7 are alkyl, aryl, or a combination thereof; and each X can independently be O, N, Se, S, alkylene, or a combination thereof; and (d)
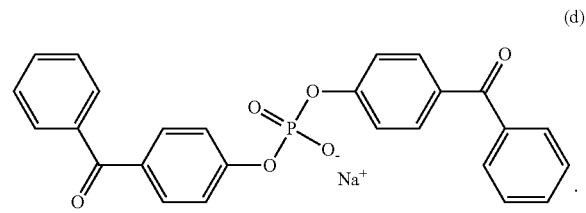

In a particular embodiment, the crosslinking agent can be bis(4-benzoylphenyl) phosphate.

In some embodiments, the photoactivatable crosslinking agent can be ionic, and can have good solubility in an aqueous composition, such as the first and/or second coating composition. Thus, in some embodiments, at least one ionic photoactivatable crosslinking agent is used to form the coating. In some cases, an ionic photoactivatable crosslinking agent can crosslink the polymers within the second coating layer which can also improve the durability of the coating.

Any suitable ionic photoactivatable crosslinking agent can be used. In some embodiments, the ionic photoactivatable crosslinking agent is a compound of formula I: X1-Y—X2 where Y is a radical containing at least one acidic group, basic group, or a salt of an acidic group or basic group. X1 and X2 are each independently a radical containing a latent photoreactive group. The photoreactive groups can be the same as those described herein. Spacers can also be part of X1 or X2 along with the latent photoreactive group. In some embodiments, the latent photoreactive group includes an aryl ketone or a quinone.

The radical Y in formula I provides the desired water solubility for the ionic photoactivatable crosslinking agent. The water solubility (at room temperature and optimal pH) is at least about 0.05 mg/ml. In some embodiments, the solubility is about 0.1 to about 10 mg/ml or about 1 to about 5 mg/ml.

In some embodiments of formula I, Y is a radical containing at least one acidic group or salt thereof. Such a photoactivatable crosslinking agent can be anionic depending upon the pH of the coating composition. Suitable acidic groups include, for example, sulfonic acids, carboxylic acids, phosphonic acids, and the like. Suitable salts of such groups include, for example, sulfonate, carboxylate, and phosphate salts. In some embodiments, the ionic crosslinking agent includes a sulfonic acid or sulfonate group. Suitable counter ions include alkali, alkaline earths metals, ammonium, protonated amines, and the like.

For example, a compound of formula I can have a radical Y that contains a sulfonic acid or sulfonate group; X1 and X2 can contain photoreactive groups such as aryl ketones. Such compounds include 4,5-bis(4-benzoylphenylmethyleneoxy) benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,278,018 (to Swan). The counter ion of the salt can be, for example, ammonium or an alkali metal such as sodium, potassium, or lithium.

In other embodiments of formula I, Y can be a radical that contains a basic group or a salt thereof. Such Y radicals can include, for example, an ammonium, a phosphonium, or a sulfonium group. The group can be neutral or positively charged, depending upon the pH of the coating composition. In some embodiments, the radical Y includes an ammonium group. Suitable counter ions include, for example, carboxylates, halides, sulfate, and phosphate. For example, compounds of formula I can have a Y radical that contains an ammonium group; X1 and X2 can contain photoreactive groups that include aryl ketones. Such photoactivatable crosslinking agents include ethylenebis(4-benzoylbenzyldimethylammonium) salt; hexamethylenebis (4-benzoylbenzyldimethylammonium) salt; 1,4-bis(4-benzoylbenzyl)-1,4-dimethylpiperazinediium) salt, bis(4-benzoylbenzyl) hexamethylenetetraminediium salt, bis[2-(4-benzoylbenzyldimethylammonio)ethyl]-4-benzoylbenzylmethylammonium salt; 4,4-bis(4-benzoylbenzyl)morpholinium salt; ethylenebis[(2-(4-benzoylbenzyldimethylammonio)ethyl)-4-benzoylbenzylmethylammonium]salt; and 1,1,4,4-tetrakis (4-benzoylbenzyl)piperzinediium salt. See U.S. Pat. No. 5,714,360 (to Swan et al.). The counter ion is typically a carboxylate ion or a halide. On one embodiment, the halide is bromide.

In other embodiments, the ionic photoactivatable crosslinking agent can be a compound having the formula:

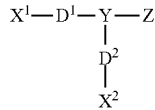

wherein X1 includes a first photoreactive group; X2 includes a second photoreactive group; Y includes a core molecule; Z includes at least one charged group; D1 includes a first degradable linker; and D2 includes a second degradable linker. Additional exemplary degradable ionic photoactivatable crosslinking agents are described in US Patent Application Publication US 2011/0144373 (Swan et al., "Water Soluble Degradable Crosslinker"), the disclosure of which is incorporated herein by reference.

In some aspects a non-ionic photoactivatable crosslinking agent can be used. In one embodiment, the non-ionic photoactivatable crosslinking agent has the formula XR1R2R3R4, where X is a chemical backbone, and R1, R2, R3, and R4 are radicals that include a latent photoreactive group. Exemplary non-ionic crosslinking agents are described, for example, in U.S. Pat. Nos. 5,414,075 and 5,637,460 (Swan et al., "Restrained Multifunctional Reagent for Surface Modification"). Chemically, the first and second photoreactive groups, and respective spacers, can be the same or different.

In other embodiments, the non-ionic photoactivatable crosslinking agent can be represented by the formula:

PG2-LE2-X-LE1-PG1 wherein PG1 and PG2 include, independently, one or more photoreactive groups, for example, an aryl ketone photoreactive group, including, but not limited to, aryl ketones such as acetophenone, benzophenone, anthraquinone, anthrone, anthrone-like heterocycles, their substituted derivatives or a combination thereof; LE1 and LE2 are, independently, linking elements, including, for example, segments that include urea, carbamate, or a combination thereof; and X represents a core molecule, which can be either polymeric or non-polymeric, including, but not limited to a hydrocarbon, including a hydrocarbon that is linear, branched, cyclic, or a combination thereof; aromatic, non-aromatic, or a combination thereof; monocyclic, polycyclic, carbocyclic, heterocyclic, or a combination thereof benzene or a derivative thereof; or a combination thereof. Other non-ionic crosslinking agents are described, for example, in Publ. No. US 2012/0149934 (to Kurdyumov, "Photocrosslinker"), the disclosure of which is incorporated herein by reference.

Further embodiments of non-ionic photoactivatable crosslinking agents can include, for example, those described in US Pat. Publication 2013/0143056 (Swan et al., "Photo-Vinyl Linking Agents"), the disclosure of which is incorporated herein by reference. Exemplary crosslinking agents can include non-ionic photoactivatable crosslinking agents having the general formula R1-X—R2, wherein R1 is a radical comprising a vinyl group, X is a radical comprising from about one to about twenty carbon atoms, and R2 is a radical comprising a photoreactive group.

A single photoactivatable crosslinking agent or any combination of photoactivatable crosslinking agents can be used in forming a coating. In some embodiments, at least one nonionic crosslinking agent such as tetrakis(4-benzoylbenzyl ether) of pentaerythritol can be used with at least one ionic crosslinking agent. For example, at least one non-ionic photoactivatable crosslinking agent can be used with at least one cationic photoactivatable crosslinking agent such as an ethylenebis(4-benzoylbenzyldimethylammonium) salt or at least one anionic photoactivatable crosslinking agent such as 4,5-bis(4-benzoyl-phenylmethyleneoxy) benzene-1,3-disulfonic acid or salt. In another example, at least one nonionic crosslinking agent can be used with at least one cationic crosslinking agent and at least one anionic crosslinking agent. In yet another example, a least one cationic crosslinking agent can be used with at least one anionic crosslinking agent but without a non-ionic crosslinking agent.

An exemplary crosslinking agent is disodium 4,5-bis[(4-benzoylbenzyl)oxy]-1,3-benzenedisulfonate (DBDS). This reagent can be prepared by combining 4,5-Dihydroxylbenzyl-1,3-disulfonate (CHBDS) with 4-bromomethylbenzophenone (BMBP) in THF and sodium hydroxide, then refluxing and cooling the mixture followed by purification and recrystallization (also as described in U.S. Pat. No. 5,714,360, incorporated herein by reference).

Further crosslinking agents can include the crosslinking agents described in U.S. Pat. No. 8,487,137 (to Guire et al.) and U.S. Pat. No. 7,772,393 (to Guire et al.) the content of all of which is herein incorporated by reference.

In some embodiments, crosslinking agents can include boron-containing linking agents including, but not limited to, the boron-containing linking agents disclosed in U.S. Pat.

No. 9,410,044 (to Kurdyumov) the content of which is herein incorporated by reference. By way of example, linking agents can include borate, borazine, or boronate groups and coatings and devices that incorporate such linking agents, along with related methods. In an embodiment, the linking agent includes a compound having the structure (I):

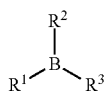

(I)

wherein R1 is a radical comprising a photoreactive group; R2 is selected from OH and a radical comprising a photoreactive group, an alkyl group and an aryl group; and R3 is selected from OH and a radical comprising a photoreactive group. In some embodiments the bonds B—R1, B—R2 and B—R3 can be chosen independently to be interrupted by a heteroatom, such as O, N, S, or mixtures thereof.

Additional agents for use with embodiments herein can include stilbene-based reactive compounds including, but not limited to, those disclosed in U.S. Pat. No. 8,487,137, entitled "Stilbene-Based Reactive Compounds, Polymeric Matrices Formed Therefrom, and Articles Visualizable by Fluorescence" by Kurdyumov et al., the content of which is herein incorporated by reference.

Additional photoreactive agents, crosslinking agents, hydrophilic coatings, and associated reagents are disclosed in U.S. Pat. No. 8,513,320 (to Rooijmans et al.); U.S. Pat. No. 8,809,411 (to Rooijmans); and 2010/0198168 (to Rooijmans), the content of all of which is herein incorporated by reference.

Natural polymers can also be used to form a hydrophilic base coat. Natural polymers include polysaccharides, for example, polydextrans, carboxymethylcellulose, and hydroxymethylcellulose; glycosaminoglycans, for example, hyaluronic acid; polypeptides, for example, soluble proteins such as collagen, albumin, and avidin; and combinations of these natural polymers. Combinations of natural and synthetic polymers can also be used.

In some instances a tie layer can be used to form a hydrophilic base layer. In yet other instances the tie layer can be added to a hydrophilic base layer. The tie layer can act to increase the adhesion of the hydrophilic base layer to a substrate. In other embodiments, the tie layer can act to increase adhesion of a hydrophobic active agent to a hydrophilic base layer. Exemplary ties layers include, but are not limited to silane, butadiene, polyurethane and parylene. Silane tie layers are described in US Patent Publication 2012/0148852 (to Jelle, et al.), the content of which is herein incorporated by reference.

In exemplary embodiments, the hydrophilic base layer can include tannic acid, polydopamine or other catechol containing materials.

The insertion tool can be used in a system with a balloon catheter. Balloon catheters are commonly used in angioplasty procedures for the treatment of arteries that are diseased. Balloon angioplasty generally involves the dilation or reopening of blocked intraluminal channels. Balloon catheter constructions are well known in the art and are described in various documents, for example, U.S. Pat. Nos. 4,195,637, 5,041,089, 5,087,246, 5,318,587, 5,382,234, 5,571,089, 5,776,101, 5,807,331, 5,882,336, 6,394,995, 6,517,515, 6,623,504, 6,896,842, 7,163,523, and 8,951,545.

With reference to FIG. 14, a balloon catheter (portions thereof not drawn to scale) generally includes four portions: the balloon 1212, catheter shaft 1210, guidewire (not shown), and manifold 1214. The inflatable balloon 1212 is typically attached to a distal section of the flexible catheter shaft 2010, and catheter shaft 2010 can include one or more aperture(s) 1213 that allow the balloon to be inflated, such as with a liquid. The catheter shaft can extend distally a short length to a distal tip 1211. At the proximal end of the catheter shaft, there is typically the manifold 1214 which is configured to remain outside the patient and includes a guide wire port 1217 and an inflation fluid port 1216. At the manifold end, placement of the catheter can be facilitated using a guidewire. Guidewires are small and maneuverable and can facilitate movement of the balloon catheter into the body through the insertion tool and the hemostatic valve. In some arrangements, the balloon and catheter is fixed to the guidewire, which can be moved together with the guidewire. In other arrangements, the balloon and catheter are not fixed to the guidewire and can be moved in relation to one another.

The catheter body is typically flexible so that it can navigate through the arterial system when introduced into a subject. The catheter can include a more rigid portion 1215 immediately distal to the inflation port 2014. When in a straightened configuration (i.e., when the catheter body is straightened along a linear path), the catheter can have an axis "catheter axis" CA. The length ($L_1$) of balloon catheters can vary; standard lengths being in the range of about 50 cm to about 150 cm.

The balloon portion of the balloon catheter can be of various lengths ($L_2$) and a particular length can be used based on diagnosis of a patient and the size of the arterial area to be treated. Exemplary balloon lengths are in the range of about 20 mm to about 300 mm, about 25 mm to about 250 mm, or about 30 mm to about 160 mm, with "shorter" lengths being in the range of about 20 mm to about 60 mm, or about 30 mm to about 50 mm, with "longer" lengths being in the range of about 80 mm to about 300 mm, or about 100 mm to about 250 mm.

The balloon of the balloon catheter can also be of various diameters and a particular diameter can be used based on diagnosis of a patient and the relative diameter of the artery at the site to be treated. Balloon diameters are measured in an inflated state, and exemplary diameters are in the range of about 0.5 mm to about 12 mm, or about 1 mm to about 8 mm, or about 2 mm to about 7 mm. Exemplary balloon diameters are about 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, and 12.0 mm.

With reference to FIG. 15 which shows a cross sectional view from the distal end of a balloon portion, prior to inflation the balloon can be folded to a compacted configuration for delivery to the target site. The balloon can be folded around the catheter body 1301 which in turn reduces the radial profile of the balloon catheter and facilitates movement through the insertion tool and into the body. A balloon folding process may involve creating "arms" 1302 of the balloon material and folding these arms inward (towards the catheter axis) to compact the balloon material. Depending on the balloon and the folding process in a deflated folded configuration the balloon can have two or more arms, such as three, four, five, six, seven, eight, nine, ten, eleven, or twelve folded arms.

In a folded configuration, the balloon portion can have a "maximum crossing profile," which is the maximum diameter found between the distal end of the manifold (1215, FIG. 14) and the distal end (tip) of the catheter (1211, FIG.

14). For example, the maximum crossing profile may occur at one or more points along the length of the folded balloon portion, along a continuous portion of the length, along most of the length, or along all of the length. The maximum crossing profile may also occur at the point where the balloon meets (e.g., is bonded or adhered to) the catheter shaft (see points 1524 and 1526 of FIG. 17).

In an embodiment, and as shown in FIG. 15, the folded balloon has a maximum crossing profile of length $L_3$. For example, length $L_3$ may be the diameter of the folded balloon between the outer surface of a distal end 1305 of folded balloon arm and distal end 1307 of radially opposite folded balloon arm. In some embodiments, the maximum crossing profile is about 2.20 mm or less, about 2.15 mm or less, about 2.10 mm or less, about 2.05 mm or less, about 2.00 mm or less, about 1.95 mm or less, about 1.90 mm or less, or about 1.85 mm. In some embodiments, the maximum crossing profile is in the range of about 1.60 mm to about 2.20 mm, about 1.65 mm to about 2.10 mm, or about 1.70 mm to about 2.00 mm, or about 1.75 mm to about 1.90 mm. In some embodiments, the maximum crossing profile is in the range of about 1.70 mm to about 2.00 mm, or about 1.75 mm to about 1.90 mm, and the balloon length is about 100 mm or less (e.g., about 20 mm to about 100 mm), or about 60 mm or less (e.g., about 20 mm to about 100 mm).

Figure 16:
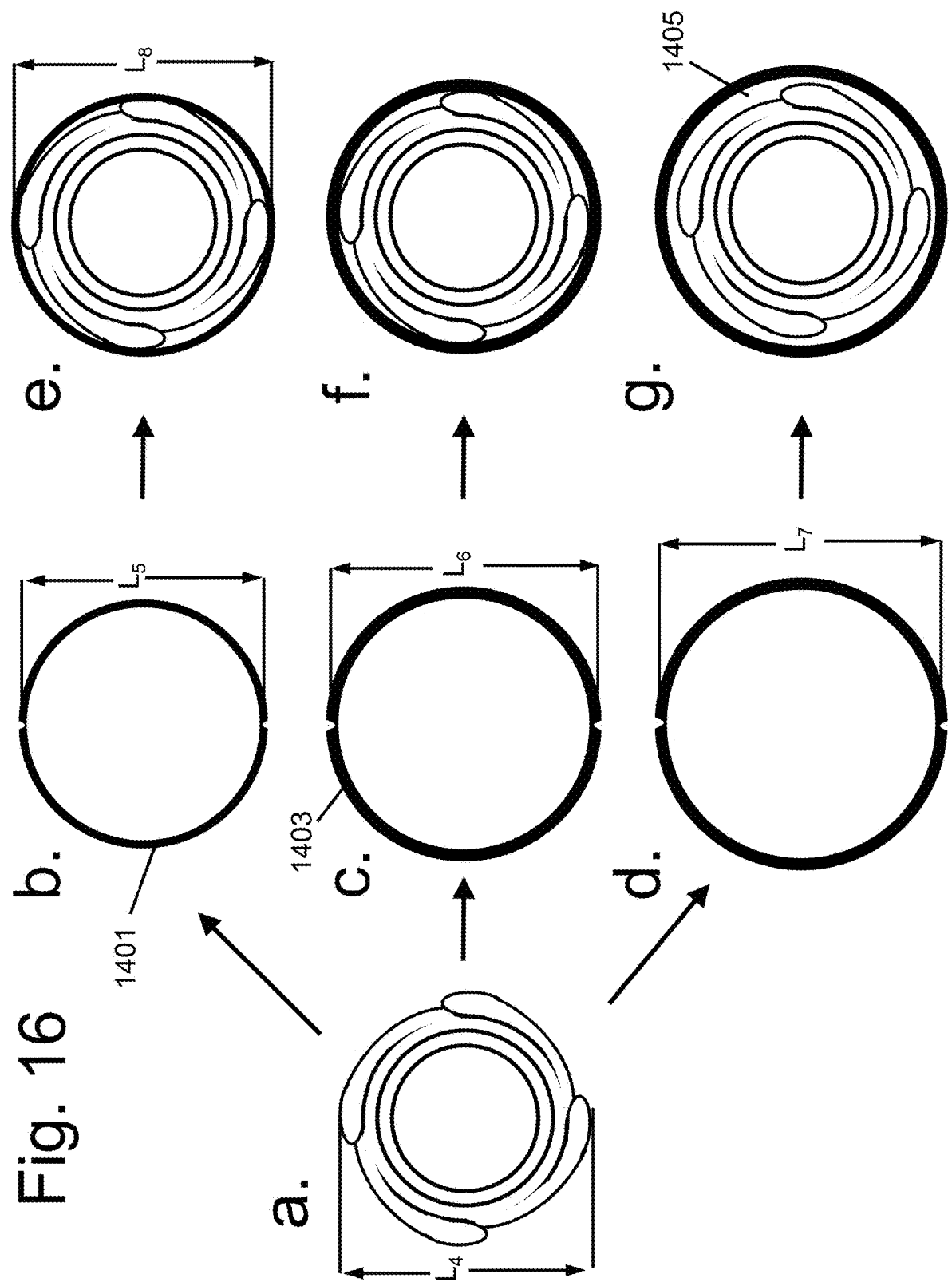
FIG. 16 are illustration of a distal end of a balloon catheter showing a balloon portion in a folded configuration and the balloon portion loaded into various insertion tool embodiments.

FIGS. 16a-16g illustrate various embodiments of the loading of a folded balloon catheter into an insertion tool, as reflected by cross sectional views from the distal end of the balloon portion and insertion tool. FIG. 16a is a folded balloon portion having a maximum crossing profile "$L_4$," such as in the range of about 1.70 mm to about 2.00 mm, or about 1.75 mm to about 1.90 mm. FIG. 16b is a cross section of an insertion tool that has an inner diameter of length $L_5$ that is not greater than the maximum crossing profile $L_4$ of the folded balloon. In some cases $L_5$ is less than $L_4$, for example $L_5$ is in the range of about 90% to about 99%, or about 95% to about 99%, of the length $L_4$. In these embodiments, the outer surface of the folded balloon will exert force upon the inner wall of the insertion tool, which can cause radial expansion of the insertion tool (e.g., deformation of the wall), further compression of the folded balloon, or both. For example, FIG. 16e shows an insertion tool (from FIG. 16b) loaded with a folded balloon causing radial expansion of the diameter of the insertion tool. In cases where $L_5$ is equal to or less than $L_4$, the wall 1401 of the insertion tool can be relatively thin, such as about less than 0.075 mm, less than 0.06 mm, or less than 0.05 mm, such as in the range of about 0.025 mm to about 0.06 mm, or about 0.025 mm to about 0.05 mm.

FIG. 16c is a cross section of an insertion tool that has an inner diameter of length $L_6$ that is at least the maximum crossing profile $L_4$ of the folded balloon, or slightly greater than $L_4$. In these embodiments, the folded balloon will fit in the inner diameter of the insertion tool with minimal or no open space between the inner wall of the insertion tool and the outer surface of folded balloon. This can be beneficial during insertion of the balloon catheter as it can minimize or prevent backflow of blood, which in turn improves safety of the procedure and can also maintain desirable balloon properties such as by minimizing drug loss and/or preventing hydration of a balloon coating (when a drug coated balloon is used). In cases where $L_6$ is equal to greater than $L_4$, the wall 1403 of the insertion tool can have a greater thickness, such as greater than about 0.025 mm, or greater than about 0.05 mm, such as in the range of about 0.05 mm to about 0.20 mm.

FIG. 16d is a cross section of an insertion tool that has an inner diameter of length $L_7$ that is greater than the maximum crossing profile $L_4$ of the folded balloon. In these embodiments, the folded balloon will fit in the inner diameter of the insertion tool and there will be some open space 1405 between the inner wall of the insertion tool and the outer surface of folded balloon. While this arrangement facilitates movement of the balloon portion of the balloon catheter within the insertion tool, preferably, the open space is limited to minimize backflow of blood. In some preferred embodiments, the maximum crossing profile of the folded balloon is about 80% or greater of the inner diameter of the insertion tool, about 82% or greater, about 84% or greater, about 86% or greater, about 88% or greater, about 90% or greater, about 92% or greater, about 94% or greater, about 96% or greater, or about 98% or greater of the inner diameter of the insertion tool, such as in the range of about 80% to about 99%, about 82% to about 99%, about 84% to about 99%, about 86% to about 99%, about 88% to about 99%, about 90% to about 99%, about 92% to about 99%, about 94% to about 99%, about 96% to about 99%, or about 98% to about 99% of the inner diameter of the insertion tool.

In a method of the disclosure, a balloon catheter can be inserted into a patient's body in a method that includes the following steps. First, (i) a balloon catheter comprising a catheter shaft and balloon portion having a length and (ii) an insertion tool for the entry of the balloon catheter into a patient's body, are provided. The insertion tool is one of the disclosure that has a proximal and distal ends along a lengthwise axis; a tubular portion extending proximally from the distal end having a length that is least the length of the balloon portion length, the tubular portion comprising: a wall, an inner diameter that can accommodate a balloon portion of a balloon catheter, a separation margin in the wall of a first lengthwise half of the tubular portion and which represents a structural weakening of, or a split in the wall in the first half; and a tab at the proximal end wherein either: (1) the tab extends from a second lengthwise half of the tubular portion, the tab having a portion at an angle skew to the lengthwise axis, or (2) the tab is in the form of a solid article comprising a concave surface that is fastened to an outer surface of the second lengthwise half of the tubular portion.

Next, the distal end of the insertion tool with balloon therein is inserted into in a hemostatic valve. After that, the tubular portion of the insertion tool and balloon catheter therein are advanced through the hemostatic valve and into the patient's body.

A portion of the proximal end of the insertion tool may remain proximal to the hemostatic valve during the insertion. With the insertion tool partially advanced through the hemostatic valve, the inflatable part of the balloon catheter can then be completely advanced through the insertion tool into the body.

Next, the tubular portion of the insertion tool is withdrawn from the hemostatic valve so as to position at least a proximal portion of the tubular portion around the catheter shaft which is proximal to the balloon portion. Next, the insertion tool is moved in relation to the balloon catheter to cause the separation margin to separate so the insertion tool can be moved away from the catheter shaft.

Alternatively, the insertion tool is placed proximal to inflatable portion of the balloon catheter, with the inflatable portion remaining protected by a separate protection sheath. The sheath can then be removed and the insertion tool then advanced over a folded inflatable part and then inserted through hemostatic valve with the balloon inside.

For insertion tool removal, force can be applied, for example, in an outward or proximal direction, to the tab of the insertion tool which causes the separation margin to separate so the insertion tool can be moved away from the catheter shaft. Alternatively the tubular portion of the insertion tool can be withdrawn all the way over the catheter shaft to the proximal hub, which can function as a wedge and cause the separation margin to separate, which in turn allows the insertion tool to be moved away from the catheter shaft. Alternatively, the user can move the insertion tool to the proximal portion of the balloon catheter which has an OD that is larger than the ID of the tubular part of the insertion tool. This portion of the catheter can then function as a wedge and can cause the insertion tool to split open along the separation margin.

Treatment of a plaque region is described in greater detail. The balloon portion of the balloon catheter can be inserted into the insertion tool and advanced through the hemostatic valve in an unexpanded state. A flared opening of the insertion tool may prevent loss of any coating on the balloon portion. After the guidewire is moved to a location for plaque treatment, the balloon portion is moved through the hemostatic valve, and the catheter with balloon portion is then fed over the guidewire until the balloon reaches the site for plaque treatment. The balloon can then be inflated at the plaque site thereby providing treatment. The manifold can also control the fluid introduction within shaft for expansion of the balloon.

The balloon is typically inflated using a fluid, which is injected through an inflation port. The mechanics of fluid transfer and introduction within balloons vary according to the specific design of the catheter, and are well known in the art.

In some embodiments, bioactive agent is associated with the surface of the balloon portion of the balloon catheter. The bioactive agent can be releasably associated with the balloon portion, or non-releasably associated with the balloon portion in a manner that it presents bioactive agent to body tissue. In some embodiments the balloon portion comprises a coating, such as hydrophilic or hydrogel coatings described herein, that can modulate the release of bioactive agent. For example, the bioactive agent can be present within and releasable from the polymeric material coated on the surface of the balloon. A polymeric coating may also be applied over a drug or drug containing layer to serve as a top coat which modulates the release of the bioactive agent.

Exemplary bioactive agents include, but are not limited to, antibiotics, anti-inflammatory agents, anti-proliferative agents, immunomodulatory agents, anti-mitotics and anesthetics. Examples of bioactive agents that could be released or presented from the balloon portion include sirolimus (rapamycin), analogs of rapamycin ("rapalogs"), tacrolimus, everolimus, zotarolimus, temsirolimus, pimecrolimus, ridaforolimus, paclitaxel, taxane, dexamethasone, betamethasone, paclitaxel, vinblastine, vincristine, vinorelbine, poside, teniposide, dactinomycin (actinomycin D), daunorubicin, doxorubicin, idarubicin, anthracyclines, mitoxantrone, bleomycins, plicamycin (mithramycin), mitomycin, mechlorethamine, cyclophosphamide and its analogs, melphalan, chlorambucil, ethylenimines and methylmelamines, alkyl sulfonates-busulfan, nirtosoureas, carmustine (BCNU) and analogs, streptozocin, trazenes-dacarbazinine, methotrexate, fluorouracil, floxuridine, cytarabine, mercaptopurine, thioguanine, pentostatin, 2-chlorodeoxyadenosine, cisplatin, carboplatin, procarbazine, hydroxyurea, mitotane, aminoglutethimide, estrogen, heparin, synthetic heparin salts, tissue plasminogen activator, streptokinase, urokinase, aspirin, dipyridamole, ticlopidine, clopidogrel, abciximab, breveldin, cortisol, cortisone, fludrocortisone, prednisone, prednisolone, 6U-methylprednisolone, triamcinolone, aspirin, acetaminophen, indomethacin, sulindac, etodalac, tolmetin, diclofenac, ketorolac, ibuprofen and derivatives, mefenamic acid, meclofenamic acid, piroxicam, tenoxicam, phenylbutazone, oxyphenthatrazone, nabumetone, auranofin, aurothioglucose, gold sodium thiomalate, cyclosporine, tacrolimus (FK-506), azathioprine, mycophenolate mofetil, vascular endothelial growth factor (VEGF), fibroblast growth factor (FGF); angiotensin receptor blocker; nitric oxide donors; anti-sense oligionucleotides and combinations thereof; cell cycle inhibitors, mTOR inhibitors, and growth factor signal transduction kinase inhibitors.

Other exemplary embodiments of bioactive agents include, but are not limited to plaque-penetrating peptides such as described by She et al., J. Contr. Rel. 238:212-220, (2016), therapeutic antibodies, siRNA or microRNA (miRNA) targeting atherosclerosis (e.g., Feinberg et al., Circ Res. 118:703-20 (2016)).

Other exemplary embodiments of bioactive agents include, but are not limited to, bioactive agents for treatment of hypertension (HTN), such as guanethidine.

In a particular embodiment, the bioactive agents are selected from the group consisting of paclitaxel, sirolimus (rapamycin) and mixtures thereof.

In some embodiments, bioactive agent is associated with the balloon portion, and the bioactive agent is within, or in the form of microparticulates, that are associated with the balloon portion. When the second tube is expanded, the microparticulates can be released or dissociated from the balloon surface. Exemplary coatings include those including hydrophilic polymers, and those including degradable polymers. Following release from the balloon portion, the microparticulates can become associated with tissue and release bioactive agent.

In one embodiment, the plaque treatment portion comprises a flexible hydrogel coating and microparticulates associated with the balloon coating. The microparticulates may be associated with the coating in a non-homogenous manner, for example, the microparticulates can be associated with the flexible hydrogel coating (a) near the surface of the flexible hydrogel, coating, (b) predominantly near the flexible hydrogel coating/surface, or (c) homogenously distributed in the flexible hydrogel coating. Upon visualization, microparticulates that are marginally embedded in a flexible hydrogel coating may appear to be stuck to the coating surface. Exemplary balloon coatings including microparticulates with bioactive agent (e.g., paclitaxel) are described in U.S. Pat. Nos. 8,951,545 and 9,669,192.

In one embodiment the balloon comprises a flexible hydrogel coating and on top a coating comprising a bioactive agent and an excipient. The excipient can function as a release agent or as an agent enhancing the drug transfer to the tissue to be treated. The excipient can be a polycation.

Microparticulates can be particulate components that include bioactive agent, and which are releasable from the surface of balloon portion. The microparticulates can be any three-dimensional particle having a size (e.g., in the range of about 100 nm to about 10 μm) and shape (spherical, or substantially spherical, non-spherical shapes or irregular shape, such as rod-like, filament-like, sliver-like, or needle-like shapes) sufficient to be associated with the surface via coating materials, and then dissociated upon its expansion of the balloon.

Microparticluates can comprise biocompatible materials that incorporate and/or encapsulate bioactive agent. These biocompatible materials can be biodegradable polymers (PLA, PLGA, etc.), (semi) solid lipids, biosilica, etc.

Microparticulates that are formed solely of one or more bioactive agents can be associated with the surface of the balloon and released to target tissue in vivo. In other words, the microparticulates can be formed substantially or entirely of one or more bioactive agents, and an excipient substance that may otherwise control release of the bioactive agent from the microparticulates is not required. A microparticulate that is formed entirely or almost entirely (e.g., allowing for trace amounts of one or more other components) of a bioactive agent may be referred to herein as a "neat" microparticulate.

The bioactive agent can be in amorphous form, in crystalline form or any mixture thereof.

For example, the preparation of paclitaxel microparticles has been described in U.S. Pat. No. 6,610,317. Commonly assigned U.S. application Ser. No. 14/280,054 (U.S. 2014/0343491; Slager) and U.S. application Ser. No. 14/303,309 (U.S. 2015/0017219; Slager et al.) describes the preparation of macrolide particulates having desirable shapes and sizes using various solvent(s) and/or processing techniques.

What is claimed is:

1. An insertion tool configured to facilitate entry of a balloon portion of a balloon catheter into a patient's body through a hemostatic valve, the insertion tool comprising proximal and distal ends;
   a tubular portion extending proximally from the distal end along a lengthwise axis, the tubular portion having a length that is at least a length of the balloon portion of the balloon catheter to be inserted and a tubular portion outer diameter, the tubular portion comprising:
      a wall, a proximal end, an inner diameter that can accommodate the balloon portion of the balloon catheter, first and second separation margins in the wall of the tubular portion comprising structural weakenings of or splits in the wall of the tubular portion, wherein the first and second separation margins define first and second lengthwise halves of the tubular portion; and
   a tab portion beginning at the proximal end of the tubular portion and comprising a first tab that extends from the first lengthwise half of the tubular portion and that follows a continuously curved path ending at a proximal end of the first tab, the first tab defining a first distance between the proximal end of the first tab and a point along the lengthwise axis that is nearest to the proximal end of the first tab, and a second tab that extends from the second lengthwise half of the tubular portion and that follows a continuously curved path ending at a proximal end of the second tab, the second tab defining a second distance between the proximal end of the second tab and a point along the lengthwise axis that is nearest to the proximal end of the second tab, wherein the tubular portion outer diameter is less than the first distance and the second distance, wherein the continuously curved paths of the first and second tabs have an extent of a curve in the range of 45° to 180°, and wherein the first and second tabs are able to be straightened so as to be aligned with the lengthwise axis of the tubular portion and to provide a straightened tab portion, so the tubular portion and the straightened tab portion have a constant outer diameter from the proximal end of the tool to the distal end of the tool, and, when straightened the proximal ends of the first and second tabs correspond to the proximal end of the insertion tool.

2. The insertion tool of claim 1, wherein the first and second separation margins each comprise a fissure in the wall of the tubular portion, the fissures having a depth that is at least 10% of a thickness of the wall.

3. The insertion tool of claim 2, wherein the fissures have a V shape.

4. The insertion tool of claim 1, wherein the insertion tool has one or more of the following dimensions: the length of the tubular portion in the range of about 10 mm to about 300 mm; a circumference of the tubular portion in the range of about 1.1 mm to about 32 mm; the tubular portion outer diameter in the range of about 0.35 mm to about 10 mm; an inner diameter of the tubular portion in the range of about 0.25 mm to about 5 mm; a thickness of the wall of the tubular portion in the range of about 0.05 mm to about 2.5 mm; and/or a depth of fissures in the range of about 0.025 mm to about 1 mm.

5. The insertion tool of claim 4, wherein the insertion tool has one or more of the following dimensions: the length of the tubular portion in the range of about 10 mm to about 100 mm; the circumference of the tubular portion in the range of about 2.5 mm to about 15 mm; the tubular portion outer diameter in the range of about 1.5 mm to about 5 mm; the inner diameter of the tubular portion in the range about 1 mm to about 4 mm; the thickness of the wall of the tubular portion in the range of about 0.05 mm to about 0.5 mm; and/or the depth of fissures in the range of about 0.05 mm to about 0.15 mm.

6. The insertion tool of claim 1, wherein the insertion tool comprises a material selected from the group consisting of fluorinated ethylene propylene (FEP); high and low density polyethylene (HDPE and LDPE); polytetrafluoroethylene (PTFE; Teflon); PEBAX; polyurethane; polyamide (Nylon); polyimide; and polyester.

7. The insertion tool of claim 1, wherein the tubular portion has outer and inner surfaces, wherein one or both of the surfaces is or are associated with a low friction material.

8. The insertion tool of claim 7, wherein the low friction material is a hydrophilic coating or a fluoropolymer sleeve.

9. The insertion tool of claim 1, wherein the continuously curved paths of the first and second tabs have curved tab radii in the range of about 10 mm to about 30 mm.

10. The insertion tool of claim 1, wherein the tubular portion outer diameter is in the range of about 1.5 mm to about 5 mm.

11. The insertion tool of claim 1 configured to facilitate entry of the balloon portion of the balloon catheter into vasculature of the patient, wherein when the first tab and the second tab are straightened, the insertion tool is able to be moved through the hemostatic valve in its entirety.

12. A balloon catheter insertion system comprising the insertion tool of claim 1 and a balloon catheter, wherein a balloon portion of the balloon catheter is loaded into a portion of the tubular portion of the insertion tool.

13. The balloon catheter insertion system of claim 12, wherein the balloon portion comprises a balloon in a folded configuration and having a folded balloon diameter, and the folded balloon diameter is greater than, equal to, or less than the inner diameter of the tubular portion.

14. The balloon catheter insertion system of claim 13, wherein the folded balloon diameter is less than the inner diameter of the tubular portion, and in the range of about 80% to about 99% of the inner diameter of the tubular portion.

15. A balloon catheter insertion system comprising (i) the insertion tool of claim 1 and (ii) a hemostatic valve; or (i) the insertion tool of claim 2, (ii) a balloon catheter and (iii) a hemostatic valve.

16. A method for inserting a balloon catheter in a patient's body, the method comprising steps of:
   (a) providing a (i) a balloon catheter comprising a balloon portion having a length and a catheter shaft proximal to the balloon portion, and (ii) an insertion tool according to claim 1,
   (b) inserting the distal end of the insertion tool in a hemostatic valve;
   (c) advancing the tubular portion of the insertion tool and the balloon catheter therein through the hemostatic valve and into the patient's body;
   (d) withdrawing the tubular portion of the insertion tool from the hemostatic valve so as to position at least a proximal portion of the tubular portion around the catheter shaft; and
   (e) moving the insertion tool in relation to the balloon catheter to cause the separation margins to separate so the insertion tool can be moved away from the catheter shaft.

17. The method of claim 16, where in step (e) an outward force results in of the wall of the tubular portion along the separation margins where the wall is structural weakened.

18. An insertion tool configured to facilitate entry of a balloon portion of a balloon catheter into a patient's body through a hemostatic valve, the insertion tool comprising proximal and distal ends;
   a tubular portion extending proximally from the distal end along a lengthwise axis, the tubular portion having a length that is at least a length of the balloon portion of the balloon catheter to be inserted and a tubular portion outer diameter, the tubular portion comprising:
      a wall, a proximal end, an inner diameter that can accommodate the balloon portion of the balloon catheter, first and second separation margins in the wall of the tubular portion comprising structural weakenings of or splits in the wall of the tubular portion, wherein the first and second separation margins define first and second lengthwise halves of the tubular portion; and
   a tab portion beginning at the proximal end of the tubular portion and comprising first and second tabs that are separated from each other, wherein
   the first tab extends from the first lengthwise half of the tubular portion and has a curved configuration as defined by a first radius having a first center of origin, the first center of origin radially distant to the wall of the tubular portion,
   the second tab extends from the second lengthwise half of the tubular portion and has a curved configuration as defined by a second radius having a second center of origin, the second center of origin radially distant to the wall of the tubular portion,
   wherein the tubular portion outer diameter is less than the first radius and the second radius, and
   wherein the tool is configured to facilitate entry of the balloon portion of the balloon catheter into vasculature of the patient, wherein the first tab and the second tab are able to be straightened so as to be aligned with the lengthwise axis of the tubular portion and to provide a straightened tab portion that allows the tool to be moved through the hemostatic valve in its entirety.

19. The insertion tool of claim 18 wherein the first radius, the second radius, or both the first and second radii are in the range of about 5 mm to about 35 mm, and the tubular portion outer diameter is in the range of about 0.35 mm to about 10 mm.

20. The insertion tool of claim 19 wherein the first radius, the second radius, or both the first and second radii are in the range of about 10 mm to about 30 mm, and the tubular portion outer diameter is in the range of about 1.5 mm to about 5 mm.

* * * * *